US012758189B2

(12) United States Patent
Ferin et al.

(10) Patent No.: US 12,758,189 B2
(45) Date of Patent: Oct. 13, 2026

(54) ULTRASOUND TRANSDUCER

(71) Applicant: VERMON S.A., Tours (FR)

(72) Inventors: Guillaume Ferin, Truyes (FR); Martin Flesch, Andresy (FR); Marie-Coline Dumoux, Tours (FR); David Voisin, Savonnieres (FR); Mathieu Legros, Larcay (FR); An Nguyen-Dinh, La Riche (FR)

(73) Assignee: VERMON SA, Tours (FR)

( * ) Notice: Subject to any disclaimer, the term of this patent is extended or adjusted under 35 U.S.C. 154(b) by 849 days.

(21) Appl. No.: 16/398,588

(22) Filed: Apr. 30, 2019

(65) Prior Publication Data

US 2019/0328360 A1 Oct. 31, 2019

Related U.S. Application Data

(60) Provisional application No. 62/664,605, filed on Apr. 30, 2018.

(51) Int. Cl.

*A61B 8/00* (2006.01)
*B06B 1/06* (2006.01)

(Continued)

(52) U.S. Cl.

CPC .......... *A61B 8/4494* (2013.01); *B06B 1/0622* (2013.01); *G01S 15/8915* (2013.01); *H04R 17/00* (2013.01); *H10N 30/50* (2023.02)

(58) Field of Classification Search

None

See application file for complete search history.

(56) References Cited

U.S. PATENT DOCUMENTS 4,097,835 A * 6/1978 Green ................. G01S 15/8979 367/164
4,237,399 A * 12/1980 Sakamoto .............. G11B 5/592 310/317

(Continued)

FOREIGN PATENT DOCUMENTS

CN 102138807 A * 8/2011 ............... A61B 8/00
EP 0186096 A2 7/1986

(Continued)

OTHER PUBLICATIONS

Daher, Nadim Michel, and Jesse T. Yen. "2-D array for 3-D ultrasound imaging using synthetic aperture techniques." IEEE transactions on ultrasonics, ferroelectrics, and frequency control 53.5 (2006): 912-924. (Year: 2006).*

(Continued)

*Primary Examiner* — Jonathan D Armstrong
(74) *Attorney, Agent, or Firm* — Stites & Harbison PLLC; Jeffrey A. Haeberlin

(57) ABSTRACT

An ultrasound transducer includes a first piezoelectric layer stacked on a second piezoelectric layer to form a stack. The first piezoelectric layer has one major face metallized to form a first array of electrodes and the other major face metallized to form a first ground electrode. The second piezoelectric layer has one major face metallized to form a second array of electrodes and the other major face metallized to form a second ground electrode, the second array of electrodes oriented at an angle to the first array of electrodes. The second piezoelectric layer has a thickness such that an overall thickness of the stack is equal to an uneven number of half-wavelengths of an acoustic wave to be generated when the first piezoelectric layer and the second piezoelectric layer are independently operated. The ultrasound trans- (Continued)

ducer also includes an acoustic impedance adaptation layer, an acoustic damping layer, and a stiffener.

1 Claim, 16 Drawing Sheets

(51) Int. Cl.

| | |
|---|---|
| ***G01S 15/89*** | (2006.01) |
| ***H04R 17/00*** | (2006.01) |
| ***H10N 30/50*** | (2023.01) |

(56) References Cited

U.S. PATENT DOCUMENTS

| | | | | |
|---|---|---|---|---|
| 4,689,514 | A * | 8/1987 | Kondoh | H01L 41/042 310/317 |
| 5,184,332 | A * | 2/1993 | Butler | H04R 17/00 181/182 |
| 5,209,126 | A | 5/1993 | Grahn | |
| 5,335,210 | A * | 8/1994 | Bernstein | G01H 11/06 367/181 |
| 5,410,205 | A * | 4/1995 | Gururaja | B06B 1/0614 310/334 |
| 5,450,747 | A * | 9/1995 | Flechsig | G11B 33/10 310/366 |
| 5,736,808 | A * | 4/1998 | Szilagyi | A42B 3/30 310/330 |
| 6,291,930 | B1 * | 9/2001 | Sager | H01L 41/0926 310/366 |
| 6,645,150 | B2 * | 11/2003 | Angelsen | B06B 1/0614 600/459 |
| 6,763,722 | B2 * | 7/2004 | Fjield | A61B 17/2202 73/644 |
| 7,009,326 | B1 * | 3/2006 | Matsuo | G10K 9/122 310/326 |
| 7,336,022 | B2 * | 2/2008 | Schuh | H01L 41/0926 310/317 |
| 7,794,401 | B2 * | 9/2010 | Kimura | A61B 8/4488 310/317 |
| 8,552,625 | B1 * | 10/2013 | Butler | H01L 41/094 310/331 |
| 8,659,211 | B1 * | 2/2014 | Butler | H01L 41/094 310/370 |
| 8,854,923 | B1 * | 10/2014 | Eyster | H04R 17/10 310/317 |
| 10,241,223 | B2 * | 3/2019 | Jin | G01V 1/24 |
| 2002/0156379 | A1 * | 10/2002 | Angelsen | H04R 17/00 600/459 |
| 2005/0140249 | A1 * | 6/2005 | Kita | H01L 41/0986 310/359 |
| 2006/0049715 | A1 * | 3/2006 | Onishi | H01L 41/042 310/317 |
| 2006/0092022 | A1 * | 5/2006 | Cehelnik | G01V 3/088 340/561 |
| 2006/0185430 | A1 * | 8/2006 | Yogeswaren | G01N 29/222 73/152.16 |
| 2008/0309200 | A1 | 12/2008 | Melandso et al. | |
| 2009/0079301 | A1 * | 3/2009 | Grohmann | B64C 3/48 29/25.35 |
| 2009/0156940 | A1 * | 6/2009 | Yen | A61B 8/483 29/25.35 |
| 2012/0119621 | A1 * | 5/2012 | Frey | H02N 2/18 310/330 |
| 2014/0261971 | A1 * | 9/2014 | Truncdemir | H10N 30/503 156/89.12 |
| 2014/0358447 | A1 * | 12/2014 | Doyle | A61B 8/085 702/19 |
| 2015/0115777 | A1 * | 4/2015 | Yun | H03H 9/02157 310/366 |
| 2016/0273351 | A1 * | 9/2016 | Fripp | B06B 1/0603 |
| 2019/0068161 | A1 * | 2/2019 | Kimura | H03H 9/02866 |
| 2020/0367858 | A1 * | 11/2020 | Baldasarre | G01S 7/52079 |
| 2022/0040735 | A1 * | 2/2022 | Chang | H01L 41/277 |

FOREIGN PATENT DOCUMENTS

| | | | | | |
|---|---|---|---|---|---|
| KR | 20020010141 | A * | 2/2002 | H01L 41/094 |
| WO | WO-02054827 | A2 * | 7/2002 | B06B 1/0614 |
| WO | 2013/065657 | A1 | 5/2013 | |
| WO | WO-2014087532 | A1 * | 6/2014 | A61B 8/145 |

OTHER PUBLICATIONS

Seo, Chi Hyung, and Jesse T. Yen. “5A-5 64x64 2-D array transducer with row-col. addressing.” 2006 IEEE Ultrasonics Symposium. IEEE, 2006. (Year: 2006).*

Savoia, A., et al. “P2B-4 crisscross 2D cMUT array: Beamforming strategy and synthetic 3D imaging results.” 2007 IEEE Ultrasonics Symposium Proceedings. IEEE, 2007. (Year: 2007).*

Logan, Andrew S., Lawrence L. Wong, and John TW Yeow. “2-D CMUT wafer bonded imaging arrays with a row-column addressing scheme.” 2009 IEEE International Ultrasonics Symposium. IEEE, 2009. (Year: 2009).*

Seo, Chi Hyung, and Jesse T. Yen. “A 256x256 2-D array transducer with row-col. addressing for 3-D rectilinear imaging.” IEEE transactions on ultrasonics, ferroelectrics, and frequency control 56.4 (2009): 837-847. (Year: 2009).*

European Patent Office, International Search Report and Written Opinion issued in corresponding Application No. PCT/IB2019/053546 mailed Sep. 4, 2019.

Yen, J.T., et al. “A Dual-Layer Transducer Array for 3-D Rectilinear Imaging,” IEEE Transactions on Ultrasonics, Ferroelectrics, and Frequency Control, vol. 56, No. 1, Jan. 2009, pp. 204-212.

Joyce, A.W., et al. “Crossed-Array Transducer for Real-Time 3D Imaging,” IEEE International Ultrasonics Symposium Proceedings, 2014, pp. 2116-2120.

Cochran, A., et al. “Multilayer Piezocomposite Ultrasonic Transducers Operating Below 50 KHZ,” IEEE Ultrasonics Symposium, 1999, pp. 953-956.

* cited by examiner

ULTRASOUND TRANSDUCER

CROSS-REFERENCE TO RELATED APPLICATIONS

This application claims the benefit of U.S. Provisional Application No. 62/664,605, filed Apr. 30, 2018, the entire disclosure of which is incorporated herein by this reference.

STATEMENT REGARDING FEDERALLY SPONSORED RESEARCH OR DEVELOPMENT

Not applicable.

THE NAMES TO PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

Field of the Invention

The present invention is directed to ultrasound imaging and therapy devices addressing different application domains from low frequency [1 MHz-6 MHz] for echocardiography to high frequency [5 MHz-20 MHz] for superficial imaging; and that are capable of handling existing imaging modalities, such as conventional B-Mode, tissue harmonic and super-harmonic imaging, Doppler and color Doppler modes, vector Doppler, elastography, photo acoustic, and acousto-optics imaging modalities. The present invention is furthermore applicable to therapeutic modalities for High Intensity Focused Ultrasound (HIFU) and drug delivery. Moreover, all these modalities are applicable to high frame rate and real time volumetric imaging (4D).

Description of the Related Art

Row-Column Addressed matrix array transducers, also commonly called RCA matrix array transducers, RCA devices, or RCA transducers are becoming more and more popular since they can be designed to comply with conventional 2D ultrasound systems without built-in micro-beamformers at the transducer side. RCA matrix array transducers use a limited number of channels (M+N independent channels, instead of M×N channels for conventional fully populated matrix arrays) typically ranged between 128 to 512. This means that each transducer plane is provided with 64 to 256 channels (half of the total number). It also noted that M might be made equal to N.

However, although the principle of operation of an RCA transducer is relatively simple, performance optimized RCA devices require particular attention to design in order to avoid undesirable acoustic responses due to: (i) the difficulty of providing an effective ground plane for the system when electrically operating the transducers in both transmit and receive modes; and (ii) issues with signal transmission through the cable due to the loss of coaxiality associated with such a transducer construction (schematically illustrated in FIG. 2, discussed below).

In principle, regular 1D, 1.75D or 2D transducers exhibit a common architecture where the active material is a polycrystalline or a monocrystalline piezoelectric material and is plated on opposite sides of its thickness with conductive material forming electrodes. Transducer elements are then drawn and interconnected to enable interfacing the transducer to a driver circuit through coaxial cables or twisted pair cables. With a coaxial cable, one electrode of each element is connected to a core conductor (e.g., a micro-cable core) and the opposite electrode of the same element is connected to a braid of the coaxial cable. With a twisted pair cable, one electrode of each element is connected to a first conductor and the opposite electrode is connected to a second conductor of twisted pair cable. This architecture allows the driver circuit to properly operate each element by applying an electrical excitation between opposites electrodes during the transmit phase and by recording the received electrical signal between the opposite electrodes. During both phases, electrical signals are driven through coaxial or twisted pair cables providing an efficient shielding and electrical impedance control of the line even at high frequencies (e.g., 20-50 MHz).

However, transducer design for ultrasonic imaging systems must follow some basic rules that are governed by high signal-to-noise ratio, electrical and acoustical cross coupling, and immunity to electromagnetic interferences. These criteria constitute fundamental requirements for imaging transducers and inherently lead to following mandatory conditions such as: i) effective conductive electrode patterns; ii) physical and effective kerfs between transducer elements; and iii) an effective ground. Most of current RCA solutions present a lack of effective ground due to design or manufacturing processes.

FIG. 1 through FIG. 6 are various views of existing designs. Commonly shown in FIG. 1 through FIG. 3 is a monolithic piezoelectric block 102 with a specific polarization direction, p, and having a first top-array of driving electrodes 104 (including an exemplary top electrode 105) on a top surface of the piezoelectric block 102 and a second bottom-array of driving electrodes 106 (including an exemplary bottom electrode 107) on an opposite bottom surface of the piezoelectric block 102. The top-array of driving electrodes 104 and the bottom-array of driving electrodes 106 are disposed in a perpendicular fashion in order to form a row-column array transducer orthogonally oriented. In FIG. 1, each electrode is electrically connected to a coaxial cable (see FIG. 2, elements 122 and 123) through a collector circuit 104 and 106. Such collector is composed of electrical tracks on an insulating substrate—typically flexible—with one extremity having a pitch equal to the plated electrode pitch and in contact with these electrodes; the other extremity of these tracks having a pitch usually larger to solder the core conductor of the coaxial cables 122. The stack is composed of only one piezoelectric layer 102 driven along its first guided Lamb wave operating at half a wavelength, i.e. λ/2 or one of its odd harmonics, i.e., 3λ/2, 5λ/2, etc.. The stack is completed on the side towards the region of interest to be imaged, by one to several acoustic impedance adaptation layers 116 typically operated at a quarter wavelength, i.e. λ/4 or its harmonics; and on the other side, an coustic damping layer 118, so called a "backing," to prevent parasitic reflections of acoustic waves, and which is attached to a stiffener 120 to provide a mechanical fixation of the whole stack. As represented by the "?" sign in FIG. 2 and FIG. 3, a ground cannot be provided herein since both main surfaces of the piezoelectric block 102 are covered by driving electrodes (i.e., the first top-array of driving electrodes 104 and the second bottom-array of driving electrodes 106), and, as a matter fact, braids, b, of coaxial cables are not connected to a ground potential which is problematic with regards to line impedance control and electromagnetic shielding of the lines.

To overcome the above ground problem, a dual-layer transducer architecture with orthogonal arrays has been proposed by Jesse T. Yen [R1]. FIG. 4 schematically shows a piezoelectric based RCA transducer architecture having a first piezoelectric layer 110 (e.g., PZT) and a second independent piezoelectric layer 112 (e.g., PVDF). The two layers are operated independently as single 1D transducers by operating the first piezoelectric layer 110 and the second piezoelectric layer 112 with respective voltage signals between Flex 1 111, Flex 2 113, and a common ground plane 114 located in between the first piezoelectric layer 110 and the backing. When one transducer is activated, the other transducer acts as a passive material where the generated or received mechanical waves propagate therethrough. Such a device is equivalent to two independent transducers assembled together. Even though this architecture allows a ground plane to be provided, the construction with two separate layers of active materials leads to intricate difficulties of acoustic optimization. The difficulties are due to the fact that, during operations, the first piezoelectric layer 110 is considered as passive backing material when the second piezoelectric layer 112 is activated, and, in turn, the second piezoelectric layer 112 is seen as passive matching layer when the first piezoelectric layer 110 is activated.

FIG. 5 schematically shows a top view of the electrical collectors Flex 1 111 and Flex 2 113 for which the electrical connections with the coaxial cables are obtained through a connector having a plurality of contacts.

Apart from RCA transducer arrays, [R3] suggests an active piezoelectric layer composed of several layers of piezocomposite material with an electrical ground plane in-between. FIG. 6 shows a 1D array which comprises a first piezoelectric layer 110 superposed by a second piezoelectric layer 112 separated by a ground plane 114. Both piezoelectric layers have opposite polarizations and the same quarter wavelength thickness (i.e. $\lambda/4$) and form a half-wavelength mode over the whole stack thickness. Each element is addressed electrically with the same signal for both electrodes at the top and at the bottom of such a stacked transducer architecture. Each top and bottom electrode are facing each other. Thus, this stack architecture is always operated (i) with the same array orientation, and (ii) the layers strictly used in parallel.

With respect to monolithic RCA designs including a unique piezoelectric layer, two main solutions are reported in the prior-art. One main solution is using add-on electronic switching circuits [R2] and shunting one electrode array to ground when transmitting or receiving with the opposite array of electrodes. This approach has been widely studied in the past through the development of sophisticated electronic switching systems, including MEMS (Micro-Electro-Mechanical Systems) switches and custom high voltage switching ASICs (Application-Specific Integrated Circuits) to allow large RCA transducer control and optimized switching operation. However, the switching duration leads to several drawbacks since it could create blind or perturbated near fields in the images because the transducer cannot receive near field backscattered acoustic waves during the switching time, and also because the switching between ground and the active signal can create electrical signal voltage differences creating artifacts in the near field image.

Adding electronic components also generates probe integration and thermal issues, and degrades signal-to-noise ratio performance since a component, having its own electrical impedance, is added between the transducer and the system front-end electronics.

The other main solution based on the FIG. 2 configuration is to provide a first electrode plane at a controlled reference voltage level (i.e., 0 V) by a driver circuit (i.e., transmit electronics) of the imaging system, while a second opposite electrode plane is kept under excitation voltage alternately using M+N individually addressed elements, including N elements on one side, and M elements on the other side. Thus, the ground plane is no longer “floating” as for the switching electronics, but with less impact on performances and integration issues. However, in that case the transmission of the reference voltage level within a cable yields to a delayed voltage establishment and is prone to electrical attenuation and perturbations. Further, efficient shielding cannot be guaranteed, as well. Still further, a blind zone in the near field of the image will still degrade the imaging capability.

Thus, the above-described strategies remain as intermediate or non-optimized solutions, and RCA transducers are therefore losing sensitivity, and are exhibiting increased cross coupling levels due to a lack of established electrical ground. Therefore, there is a need to have an imaging RCA device that overcomes drawbacks described above. Further there is a need to have a new acoustic design that preserves an effective ground plane and a proper signal transmission when transmitting and receiving through the cable, as is usually seen in conventional transducers, while preserving the advantages of RCA design for advanced imaging modes.

BRIEF SUMMARY OF THE INVENTION

In accordance with one aspect of the invention, an ultrasound transducer includes a first piezoelectric layer stacked on at least a second piezoelectric layer to form a stack. The first piezoelectric layer has one major face metallized to form a first array of electrodes and the other major face metallized to form a first ground electrode for operation as a first transducing system. The second piezoelectric layer has one major face metallized to form a second array of electrodes and the other major face metallized to form a second ground electrode for operation as a second transducing system, the second array of electrodes oriented at a first orientation angle to the first array of electrodes. The second piezoelectric layer has a thickness such that an overall thickness of the stack is equal to an uneven number of half-wavelengths of an acoustic wave to be generated when the first piezoelectric layer and the second piezoelectric layer are independently operated. The ultrasound transducer also includes an acoustic impedance adaptation layer positioned on one side of the stack, an acoustic damping layer positioned on the other side of the stack, and a stiffener positioned on the acoustic damping layer.

In one implementation, the first array of electrodes is on an outer face of the first piezoelectric layer, the second array of electrodes is on an outer face of the second piezoelectric layer, and the first ground electrode and the second ground electrode are in electrical communication at respective inner faces of the first piezoelectric layer and the second piezoelectric layer, such that the first ground electrode and the second ground electrode form a common ground. In one embodiment, the first orientation angle is 90 degrees.

In another implementation, the first ground electrode is on an outer face of the first piezoelectric layer, the first array of electrodes is on an inner face of the first piezoelectric layer, the second array of electrodes is on an inner face of the second piezoelectric layer, the second ground electrode is on an outer face of the second piezoelectric layer, and a first inner insulation layer is positioned between the first array of electrodes and the second array of electrodes. In one embodiment, the first orientation angle is 90 degrees.

In a further implementation, the first array of electrodes is on an outer face of the first piezoelectric layer, the first ground electrode is on an inner face of the first piezoelectric layer, the second array of electrodes is on an inner face of the second piezoelectric layer, the second ground electrode is on an outer face of the second piezoelectric layer, and a first inner insulation layer is positioned between the first ground electrode and the second array of electrodes. In one embodiment, the first orientation angle is 90 degrees.

In accordance with another embodiment, the ultrasound transducer may further include a third piezoelectric layer stacked between the first piezoelectric layer and the second piezoelectric layer to form the stack. In this case, the third piezoelectric layer has one major face metallized to form a third array of electrodes and the other major face metallized to form a third ground electrode for operation as a third transducing system, the third array of electrodes is oriented at a second orientation angle to the first array of electrodes, and the second orientation angle is different from the first orientation angle. Then, the first array of electrodes is on an outer face of the first piezoelectric layer and the first ground electrode is on an inner face of the first piezoelectric layer. The third array of electrodes is on a face of the third piezoelectric layer between the third piezoelectric layer and the second piezoelectric layer, and the third ground electrode is on a face of the third piezoelectric layer between the third piezoelectric layer and the first piezoelectric layer. The first ground electrode and the third ground electrode are in electrical communication, such that the first ground electrode and the third ground electrode form a common ground. The second array of electrodes is on a face of the second piezoelectric layer between the second piezoelectric layer and the third piezoelectric layer, and the second ground electrode is on an outer face of the second piezoelectric layer. A first inner insulation layer is positioned between the second array of electrodes and the third array of electrodes. The first orientation angle may be 90 degrees, and the second orientation angle may be between 0 degrees and 90 degrees.

In another implementation, the ultrasound transducer further includes both a third piezoelectric layer and a fourth piezoelectric layer, with the third piezoelectric layer between the second piezoelectric layer and fourth piezoelectric layer, and the fourth piezoelectric layer between the first piezoelectric layer and the third piezoelectric layer. In this implementation, the third piezoelectric layer has one major face metallized to form a third array of electrodes and the other major face metallized to form a third ground electrode for operation as a third transducing system, the third array of electrodes is oriented at a second orientation angle to the first array of electrodes, and the second orientation angle is different from the first orientation angle. The fourth piezoelectric layer has one major face metallized to form a fourth array of electrodes and the other major face metallized to form a fourth ground electrode for operation as a fourth transducing system, and the fourth array of electrodes is oriented at a third orientation angle to the first array of electrodes. The third orientation angle is different from the first orientation angle and the second orientation angle. In this embodiment, the first ground electrode is on an outer face of the first piezoelectric layer, and the first array of electrodes is on an inner face of the first piezoelectric layer. The fourth array of electrodes is on a face of the fourth piezoelectric layer between the fourth piezoelectric layer and the first piezoelectric layer, and the fourth ground electrode is on a face of the fourth piezoelectric layer between the fourth piezoelectric layer and the second piezoelectric layer. The third ground is on a face of the third piezoelectric layer between the third piezoelectric layer and the fourth piezoelectric layer, and the third array of electrodes is on a face of the third piezoelectric layer between the third piezoelectric layer and the second piezoelectric layer. The fourth ground electrode and the third ground electrode are in electrical communication such that the fourth ground electrode and the third ground electrode form a common ground. The second array of electrodes is on an inner face of the second piezoelectric layer, and the second ground layer is on an outer face of the second piezoelectric layer. A first inner insulation layer is positioned between the second array of electrodes and the third array of electrodes, and a second inner insulation layer is positioned between the first array of electrodes and the fourth array of electrodes. In an important implementation, the first orientation angle is 90 degrees, the second orientation angle is between 0 degrees and 90 degrees, and the third orientation angle is also be between 0 degrees and 90 degrees.

In some embodiments, the first orientation angle is 0 degrees and electrodes of the first array of electrodes and the second array of electrodes have a pitch offset or a variation in pitch, kerf, number of elements, or element size.

According to another implementation, the first array of electrodes are coaxial, semi-cylindrical curved electrodes, and the second array of electrodes are parallel linear electrodes.

In accordance with another aspect, an ultrasound system includes the ultrasound transducer described above, an imaging system, and a plurality of coaxial cables. The imaging system includes a plurality of imaging system channels, each imaging system channel for transmitting and receiving signals to corresponding electrodes of the ultrasound transducer. With respect to the plurality of coaxial cables, each coaxial cable is for carrying the signals between an imaging system channel and the corresponding electrodes of the ultrasound transducer. Further, each coaxial cable includes a center conductor and a shielding braid. Each center conductor is in electrical communication with an electrode of the first array of electrodes and the second array of electrodes. Each shielding braid is in electrical communication with a corresponding first ground electrode and second ground electrode.

In accordance with another aspect of the invention, a method of operating the ultrasound transducer described above includes: emitting, by the ultrasound transducer, acoustic waves generated by the first piezoelectric layer and the second piezoelectric layer in response to receiving signals from imaging system channels through coaxial cables on corresponding electrodes of the ultrasound transducer; and sending, by the ultrasound transducer from the electrodes through the coaxial cables to the corresponding imaging system channels, signals corresponding to acoustic waves received by the first piezoelectric layer and the second piezoelectric layer.

BRIEF DESCRIPTION OF THE DRAWINGS

Embodiment herein will hereinafter be described in conjunction with the appended drawings and illustrations provided to illustrate and not limit the scope of the claims:

DETAILED DESCRIPTION OF EXEMPLARY EMBODIMENTS OF THE INVENTION

Figure 1:
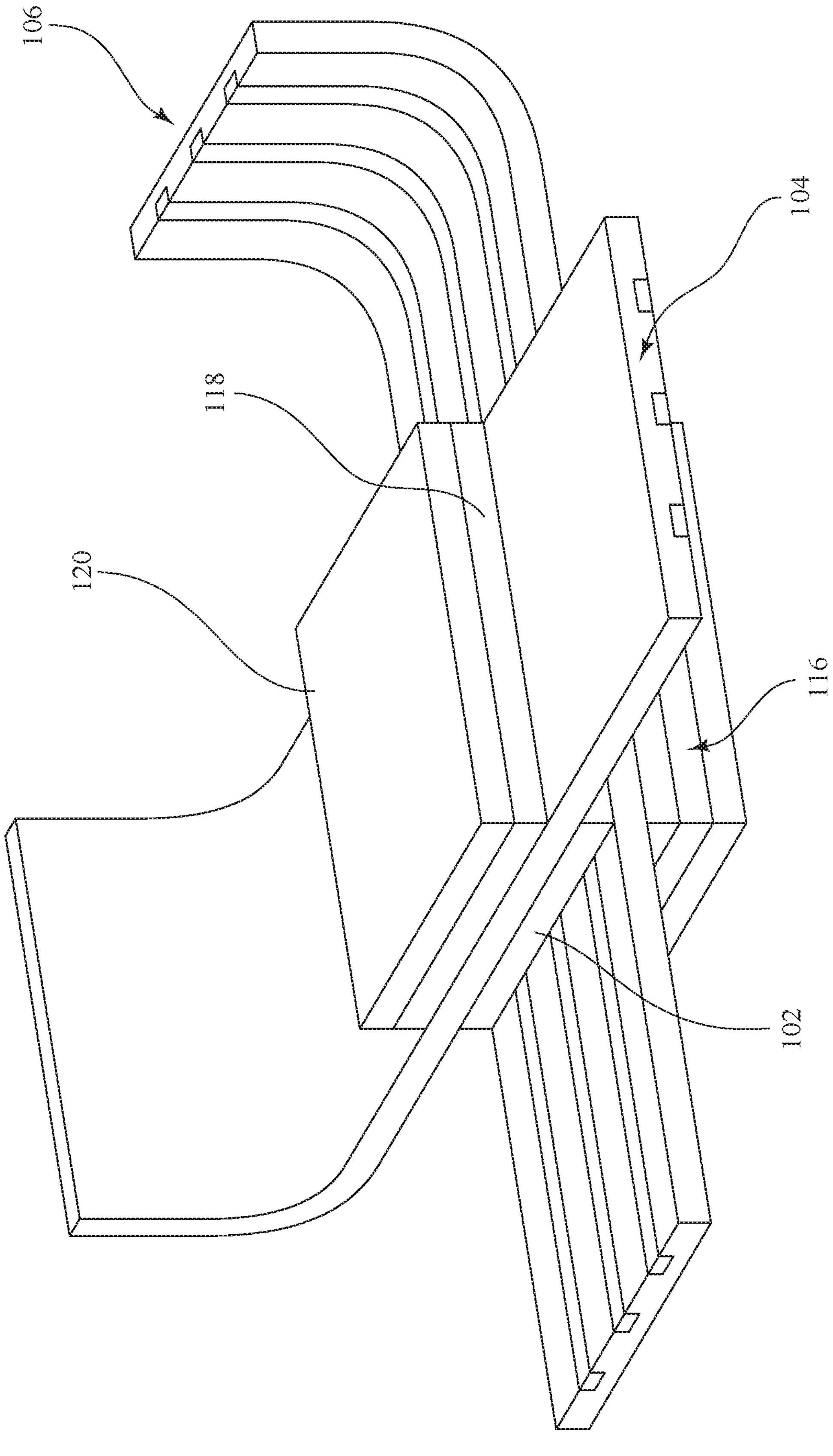
FIG. 1 (PRIOR ART)
FIG. 1 is a schematic diagram of a regular RCA transducer architecture.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a transducer" includes a plurality of such transducers, and so forth.

Unless otherwise indicated, all numbers expressing composition components, properties such as frequencies, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed subject matter.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The terms "array transducer" or "transducer array" are used herein to describe a transducer device obtained by geometric arrangement of a plurality of individual transducers (i.e., transducer elements) having dimensions compatible with desired ultrasonic beam focusing and steering features.

The terms "element transducer" or "transducer element" or "transducer" are used herein to describe an individual ultrasonic transducer component of an array transducer. Generally, an element transducer of an array transducer has planar dimensions suitable for electronic steering and focusing of ultrasonic beams. A conductive electrode is plated on each element. The conductive electrode can be either patterned by subtractive or additive processes in the case of kerfless element array; or etched together with the piezoelectric layer during the element singulation process.

Polarization direction, p, is used herein to describe the poling direction of the respective piezoelectric layer.

The term "half-wavelength mode" is used herein to describe the first mode along the transducer thickness direction operated at a half wavelength (i.e. $\lambda/2$). This half-wavelength mode is either the first symmetric guided lamb wave (so called thickness mode) or the first mode of one element wherein its lateral dimensions are slightly under its thickness (so called bar mode). The acoustic wavelength can be different for the thickness and bar mode but the half-wavelength condition remains the same to operate the first order mode. By extension, unless otherwise indicated in the description, the term "half-wavelength mode" also encompasses other higher order modes operated at any odd multiple of half-wavelength, i.e. $(2n+1)\lambda/2$, where n is any positive integer number.

The term "imaging system" is used herein to describe an apparatus which includes a signal generator, a signal processor, and a user interface. The signal generator is for generating signals for actuating transducer elements of an ultrasound transducer to generate acoustic waves. The signal processor is for processing signals generated by the transducer elements in response to acoustic waves received by the transducer elements. The signal processor further includes an image processor for generating images from the processed signals. The user interface is for displaying the generated images and for receiving additional inputs from a user of the imaging system. Such imaging systems are commercially available and known to those skilled in the art, so the details of the elements and operation of such imaging systems will not be further described herein.

Figure 2:
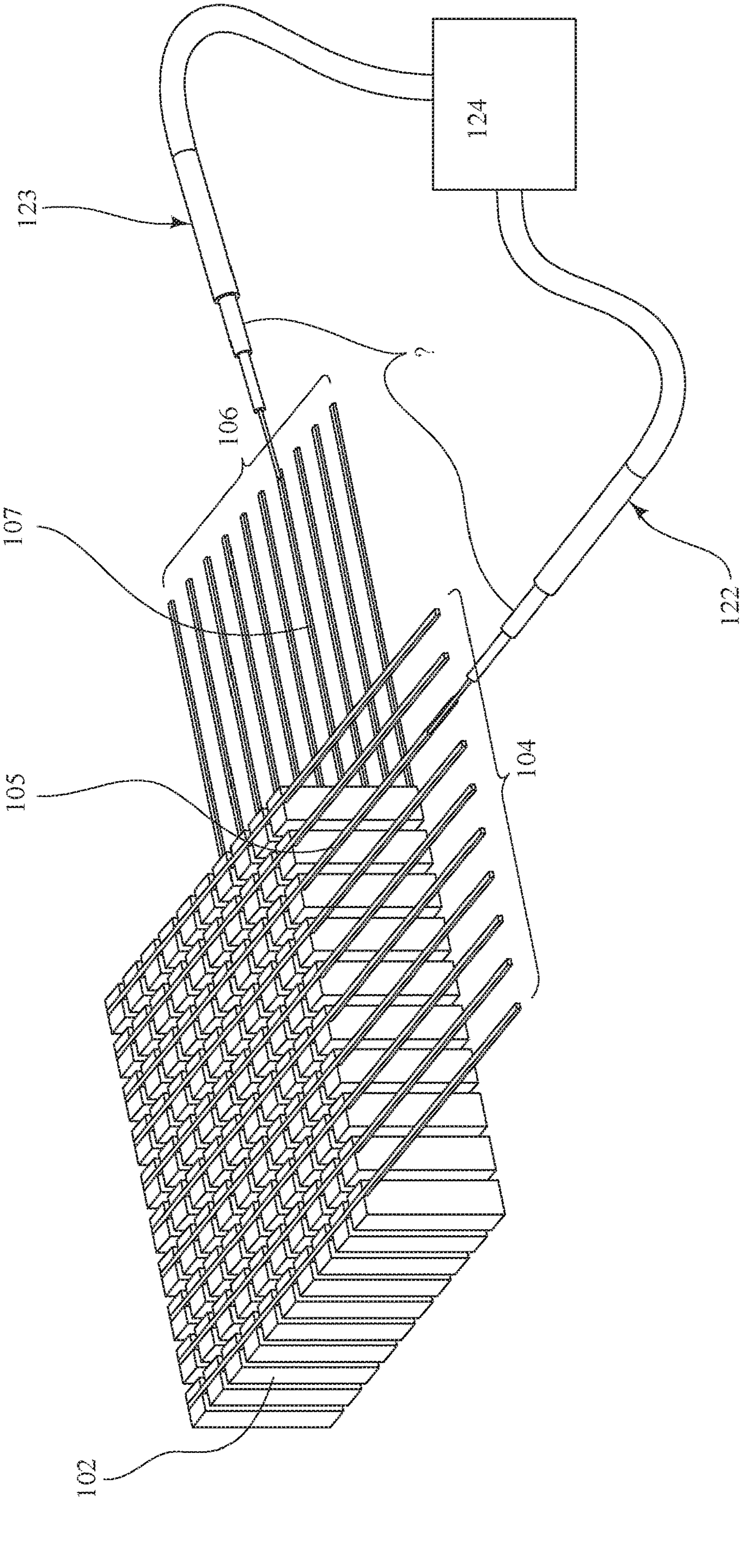
FIG. 2 (PRIOR ART)
FIG. 2 is a 3D schematic diagram of the piezoelectric parts of a regular RCA transducer without outer materials.
Figure 3:
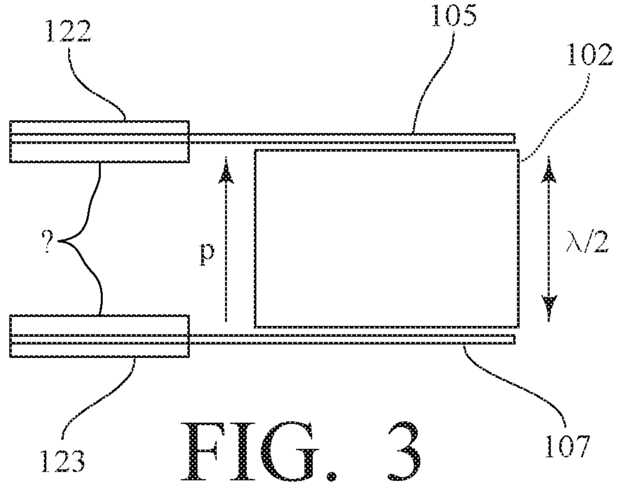
FIG. 3 (PRIOR ART)
FIG. 3 is a 2D schematic diagram of the piezoelectric parts of a regular RCA transducer without outer materials.
Figure 4:
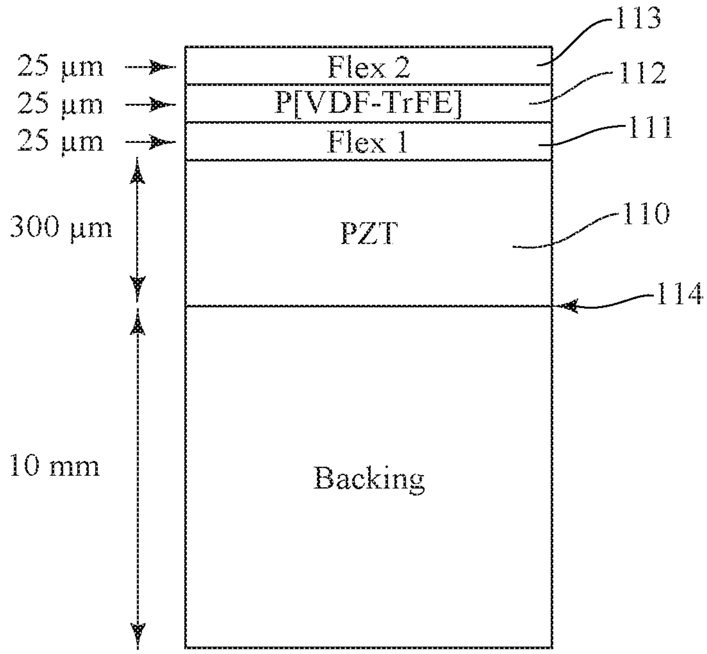
FIG. 4 (PRIOR ART)
FIG. 4 is a schematic diagrams showing a piezoelectric based RCA transducer architecture having two independent piezoelectric layers.
Figure 5:
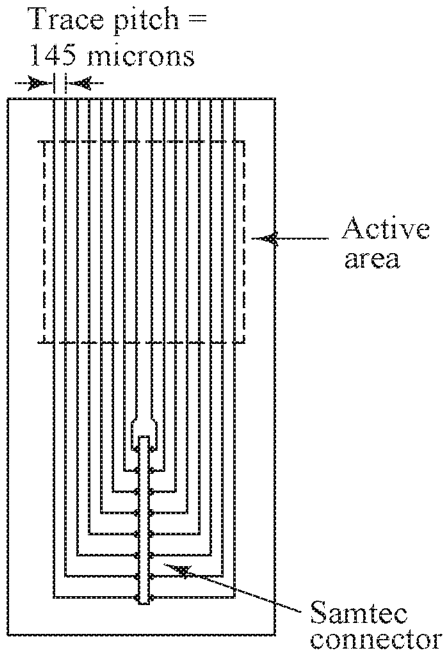
FIG. 5 (PRIOR ART)
FIG. 5 is a top view of the schematic diagram of the Flexl and Flex2 collector layers from FIG. 4.
Figure 6:
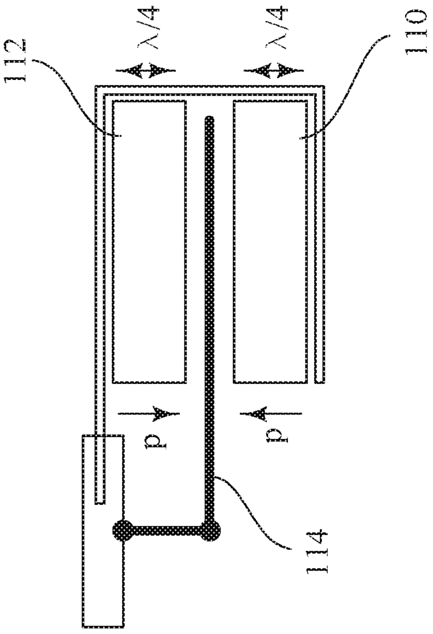
FIG. 6 (PRIOR ART)
FIG. 6 is a schematic diagram of a regular stack architecture having two piezoelectric layers connected in parallel with a common ground electrode therebetween.

Some of the exemplary embodiments described herein include new multilayered RCA transducers. These RCA transducers can be made of lead zirconate titanate (PZT), single crystals, piezoelectric polymer (e.g. PVDF: Polyvinyliden fluoride) or equivalent piezoelectric compositions such as lead-free ceramics or composites of all of the above, with no change in the principle of operation. The embodiments disclose RCA transducers that are configured to operate using phased beamformation (or beamforming) techniques, apodization, or compounding of M+N arrays, with the capability of properly driving the transducers in both transmit and receive modes. For the exemplary embodiments, the stacked multilayered transducer architecture is different as compared to the conventional stacked transducer architecture (FIG. 6) and the conventional RCA transducer architecture (FIG. 2).

In some of the exemplary embodiments, a stacked transducer is operated along at least two different array orientations as a RCA transducer. The electrical to mechanical conversion (transmit) or mechanical to electrical conversion (receive) are operated only within a portion of the whole transducer thickness between an electrode and a ground plane, meanwhile the half-wavelength mode at f0 is obtained along the whole transducer thickness. Two piezoelectric layers are used instead of one single piezoelectric layer. The piezoelectric material as well as their poling direction can be either the same or different. The resulting stack, even with orthogonal electrodes, is operated along the overall half-wavelength mode, still called half-wavelength mode.

The exemplary embodiments include stacking multiple piezoelectric layers with specific polarization directions, p, and thicknesses. In the exemplary embodiments, thicknesses of piezoelectric layers could be equal or different but the resulting overall thickness is always an odd number of half a wavelength. The resulting stack is operated along the first piezoelectric active symmetric guided mode or one of its odd harmonics corresponding to the so-called thickness or bar modes.

Figure 7:
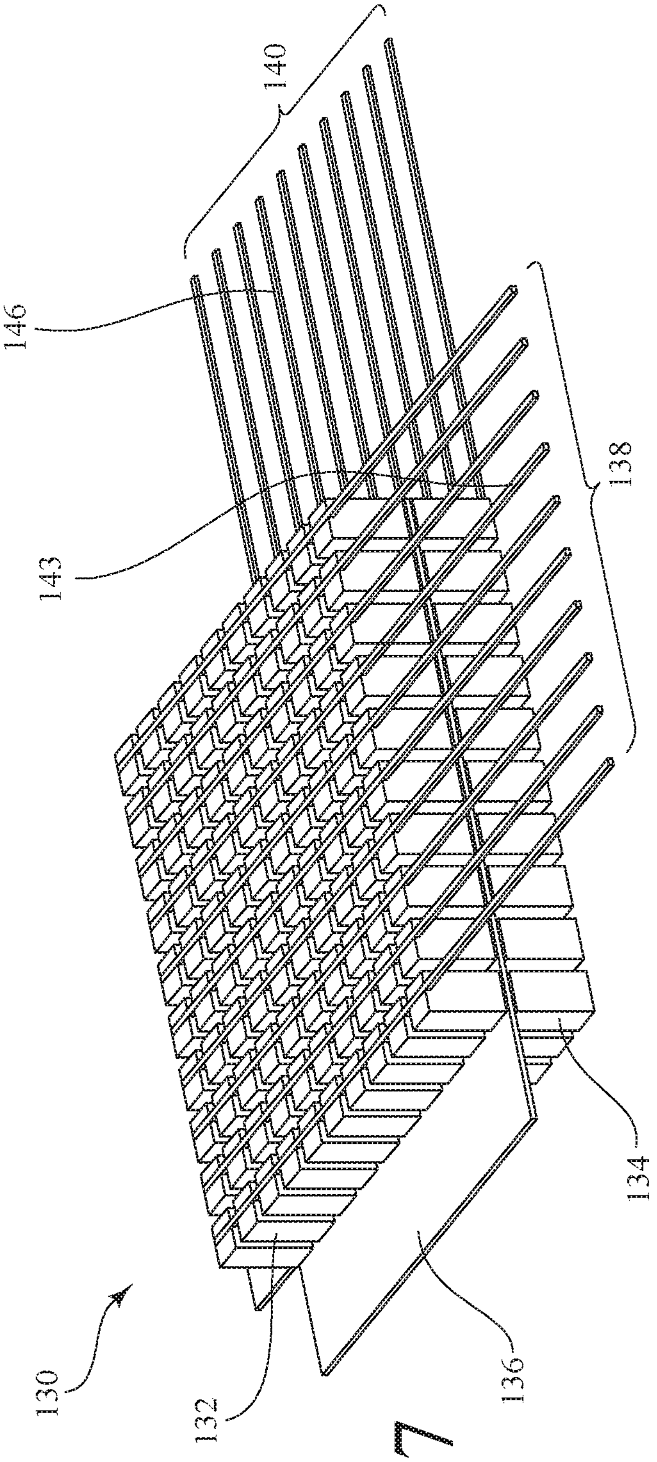
FIG. 7 is a schematic perspective of an exemplary stacked architecture RCA matrix array having orthogonal top and bottom electrodes but with an inner physical ground layer.
Figure 8:
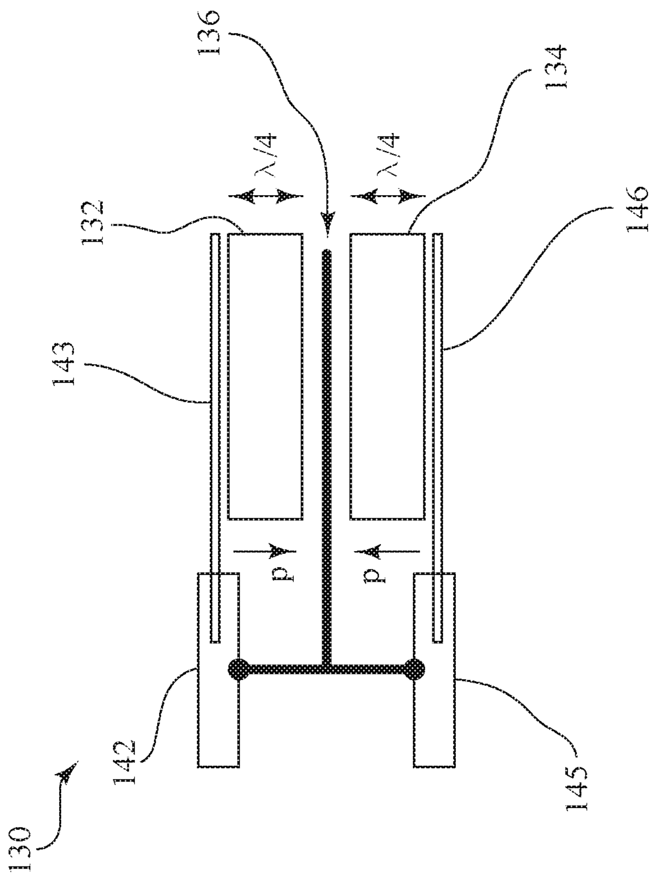
FIG. 8 is a schematic diagram of a single element transducer of the matrix array of FIG. 7.

FIG. 7 and FIG. 8 show a first exemplary embodiment of an ultrasonic transducer 130 including a first piezoelectric layer 132 and a second piezoelectric layer 134 stacked on the first piezoelectric layer 132 to form a half-wavelength mode stacked transducer. Inner faces of the first piezoelectric layer 132 and the second piezoelectric layer 134 are metallized to form a first ground electrode and a second ground electrode, respectively, which are in electrical communication with each other to collectively form a common ground electrode 136 positioned inside the stack between the first piezoelectric layer 132 and the second piezoelectric layer 134. Top and bottom outer faces of the stack are metallized and a first array of electrodes 138 (including an exemplary first electrode 143) and a second array of electrodes 140 (including an exemplary second electrode 146), respectively, are patterned thereon. The first array of electrodes 138 and the common ground electrode 136, and the second array of electrodes 140 and the common ground electrode 136 form, respectively, first and second transducing systems. The first array of electrodes 138 and the second array of electrodes 140 are arranged orthogonally to each other or in a manner so as to form an angle to each other.

To make such a device operate as a stack, an imaging system 124 (FIG. 9, FIG. 12) independently controls the transmit excitation of the piezoelectric layers to properly shape the transmission beam in phase, frequency, and amplitude. Operation in transmit mode is illustrated FIGS. 9-11.

Figure 9:
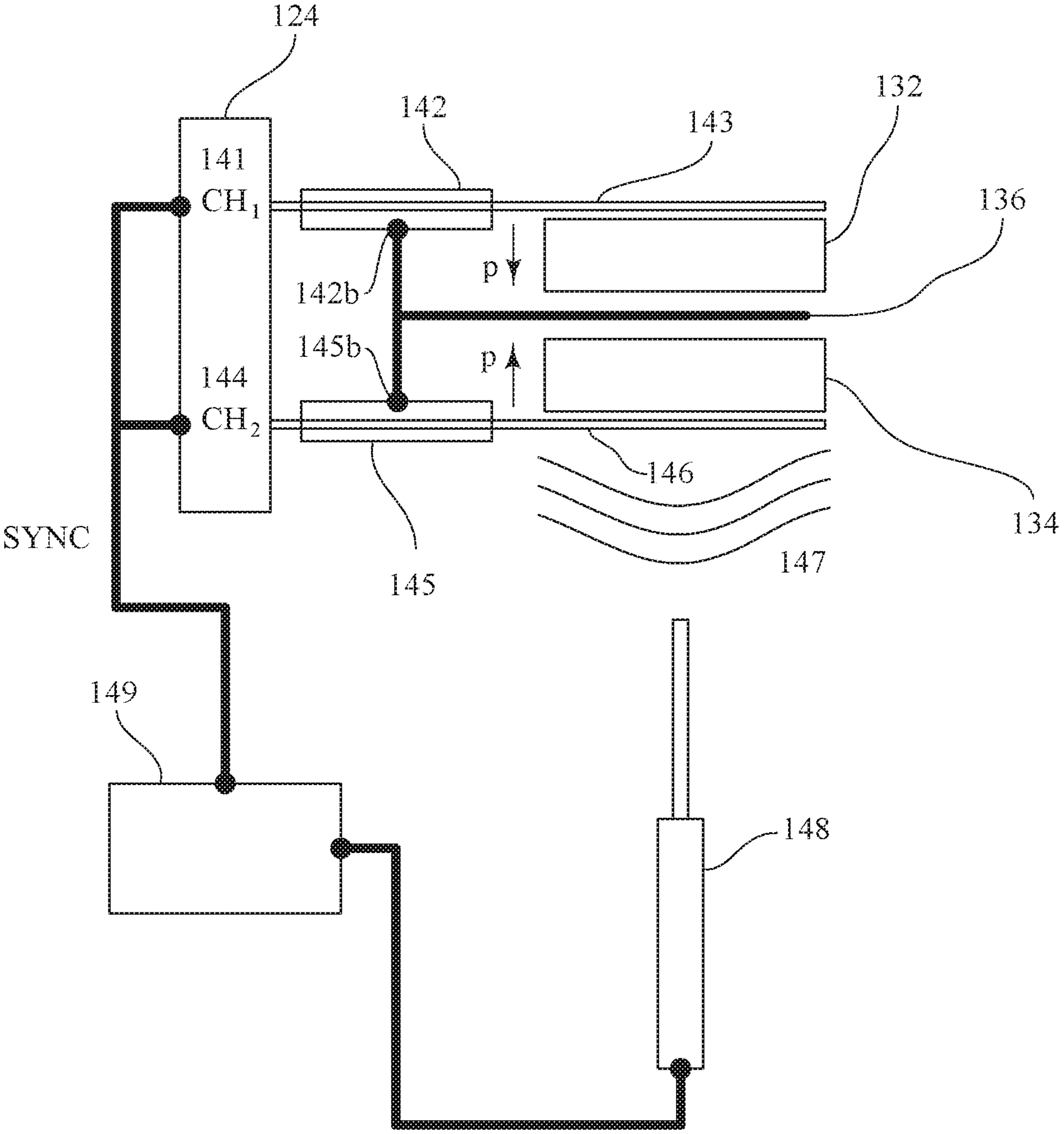
FIG. 9 is a schematic diagram of a measurement protocol which highlights the principle of operation of a stacked RCA transducer according to the invention in transmit.

FIG. 9 is a schematic of the measurement setup in transmit operation of this exemplary embodiment. The imaging system 124 (operating as a signal generator) provides pulsed signals independently for each element of the first array of electrodes 138 and the second array of electrodes 140. For example, the imaging system 124 provides a pulsed signal through a first imaging system channel 141 and a first coaxial cable 142 to the exemplary first electrode 143, and a reciprocal pulsed signal through a second imaging system channel 144 and a second coaxial cable 145 to the exemplary second electrode 146. The shielding braids **142*b* and 145*b* of the coaxial cables are connected to the ground layer 136 of the transducer providing a common voltage reference. Additional imaging system channels (not shown) and coaxial cables (not shown) provide further signals to the other elements of the first array of electrodes 138 and the second array of electrodes 140**.

As the poling direction, p, of the both piezoelectric layers 132 and 134 are opposed, a positive voltage either at the exemplary first electrode 143 or the exemplary second electrode 146 will yield to the same deformation of the first piezoelectric layer 132 (dilatation or contraction) as the second piezoelectric layer 134. If the poling direction of the both piezoelectric layers exhibited the same direction, the same deformation would be obtained with opposite signals on the top and bottom electrodes. The emitted acoustic wave 147 propagates in a medium with acoustic properties comparable to body tissues (e.g. water), and is measured by a hydrophone 148. An oscilloscope 149 synchronized with the signal generator of the imaging system 124 allows display of this measured signal. As each element is independently operated, beam forming techniques can be implemented. Basically, plane acoustic waves are obtained when all the elements of one and/or both electrodes are excited with the same signal.

Figure 10:
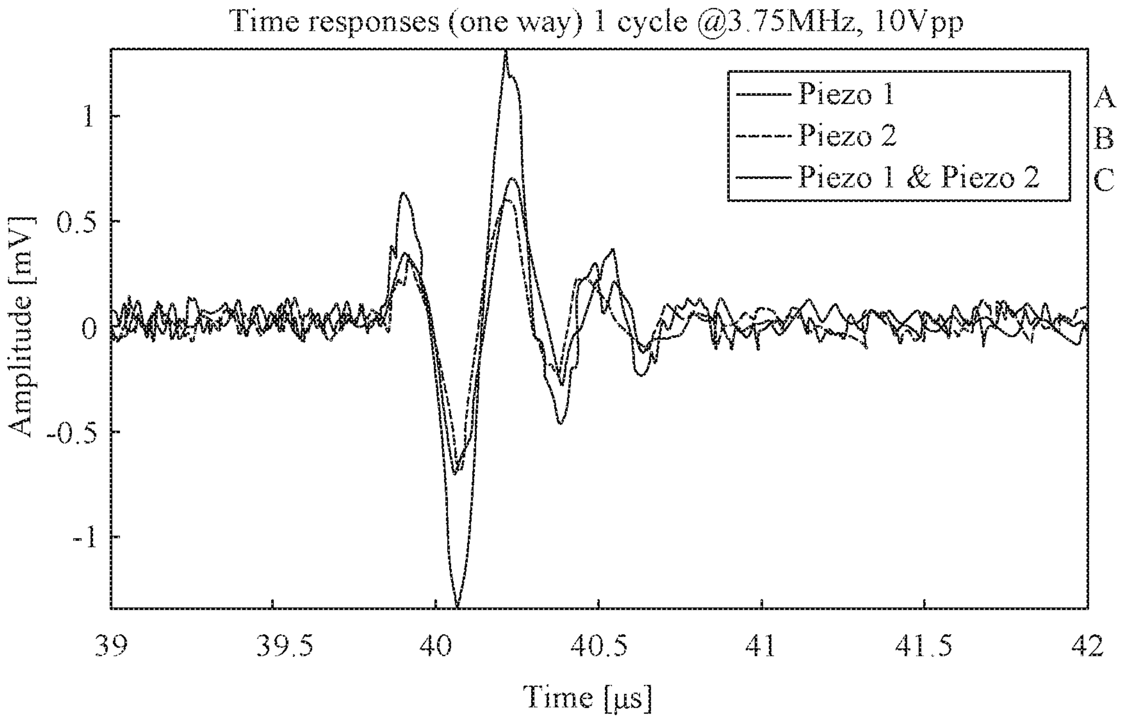
FIG. 10 and FIG. 11 are graphs illustrating the result of operation of the transducer of FIG. 9.

FIG. 10 shows exemplary signals displayed by the oscilloscope 149 when all the elements of the first array of electrodes 138 are excited with the same signal and no signal is applied to the second array of electrodes 140 (signal A); when all the elements of the second array of electrodes 140 are excited with the same signal and no signal is applied to the first array of electrodes 138 (signal B); and when all elements of both the first array of electrodes 138 and the second array of electrodes 140 are excited with the same signal (signal C). The amplitude of signal C is twice the amplitude of signal A and signal B since only half of the piezoelectric thickness is involved in the electrical to mechanical conversion for signal A and signal B in this exemplary embodiment.

Figure 11:
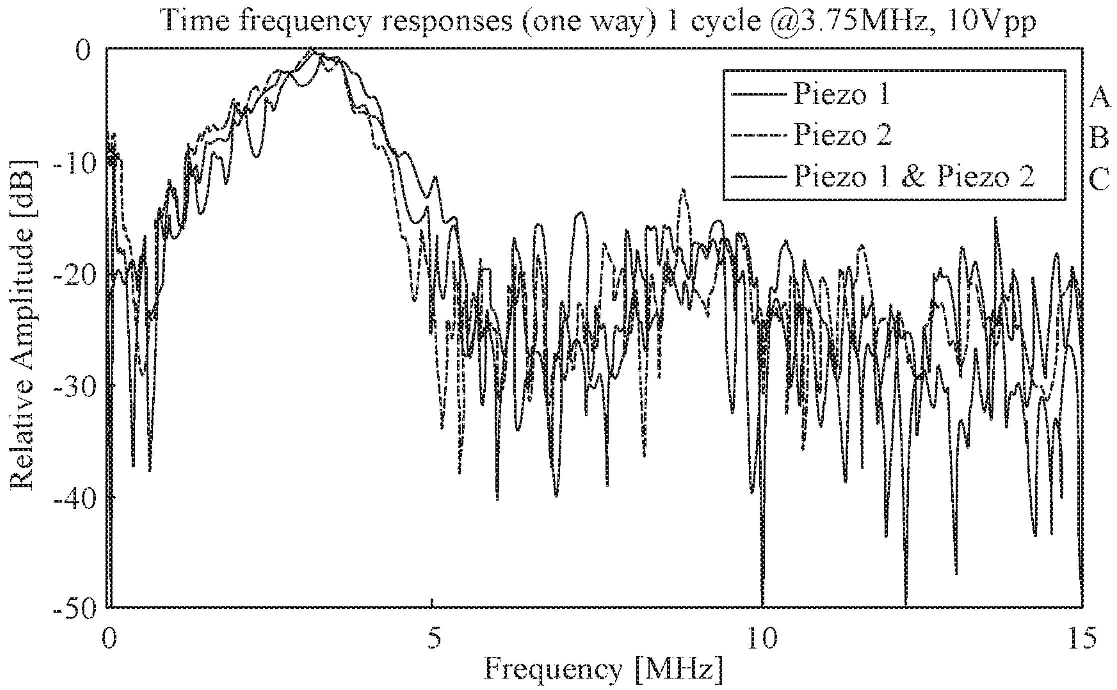

FIG. 11 shows the same measured signals as in FIG. 10 in the frequency domain. Each curve is normalized (0 dB) at its maximum, which corresponds to the central frequency of the transceiver. The central frequency and the bandwidth is the same for signal A, signal B, and signal C, showing that the transducer operates at the same half-wavelength mode even in the situation where only one of the two layers is activated.

In receive mode, the situation is different since the backscattered waves (centered at f0) will create stationary waves through the entire stack thickness. Thus, the backscattered signals are independently expressed by electromechanical conversion on all the piezoelectric layers as with a conventional single layer transducer. The received radiofrequency (RF) signals also exhibit a central frequency of fundamental frequency (f0) even if electromechanically expressed on a half (two layers), a third (three layers), a fourth (four layers), etc., of the stacked piezoelectric transducer. The principle of operation in receive is illustrated in FIGS. 12-14.

Figure 12:
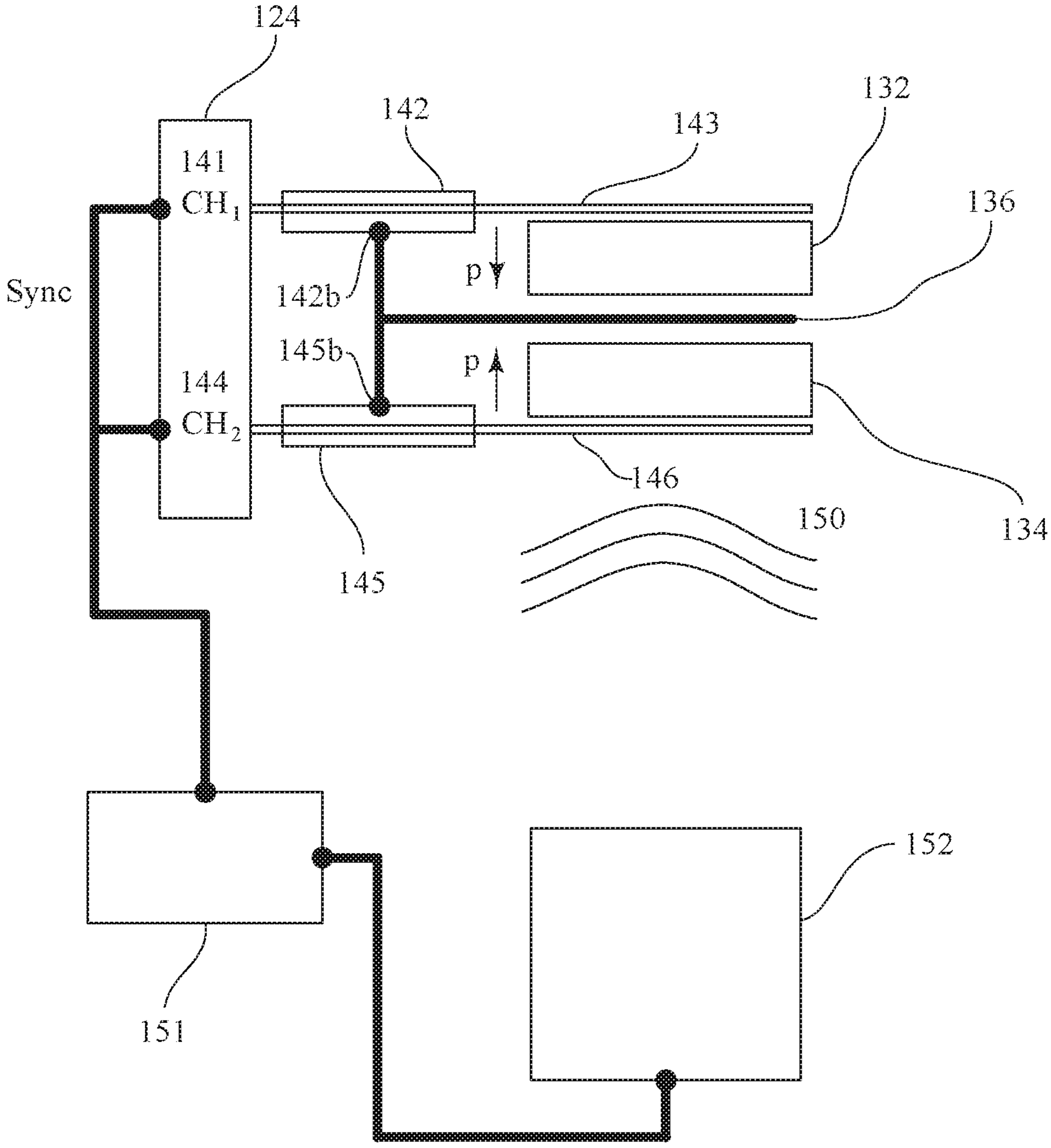
FIG. 12 is a schematic diagram of a measurement protocol which highlights the principle of operation of a stacked RCA transducer according to the invention in receive.

FIG. 12 is a schematic of the measurement setup in receive operation of this exemplary embodiment. A signal generator 151 provides a pulsed signal to a Tx hydrophone 152 which emits a plane acoustic wave 150 propagating through the medium (e.g. water) towards the transducer. The imaging system 124 independently receives signals from the exemplary first electrode 143 through the first coaxial cable 142 and the first imaging system channel 141, and reciprocal signals from the exemplary second electrode 146 through the second coaxial cable 145 and the second imaging system channel. The shielding braids **142*b* and 145*b* of the coaxial cables are connected to the ground layer 136 of the transducer providing a common voltage reference. The additional imaging system channels (not shown) and coaxial cables (not shown) allow the reception of further signals from the other elements of the first array of electrodes 138 and the second array of electrodes 140. An oscilloscope synchronized with the signal generator 151 allows the display of received signals taken from one or several coaxial cables. As the transducer receives an incoming plane acoustic wave 150**, the signal of each elements of one electrode are the same.

Figure 13:
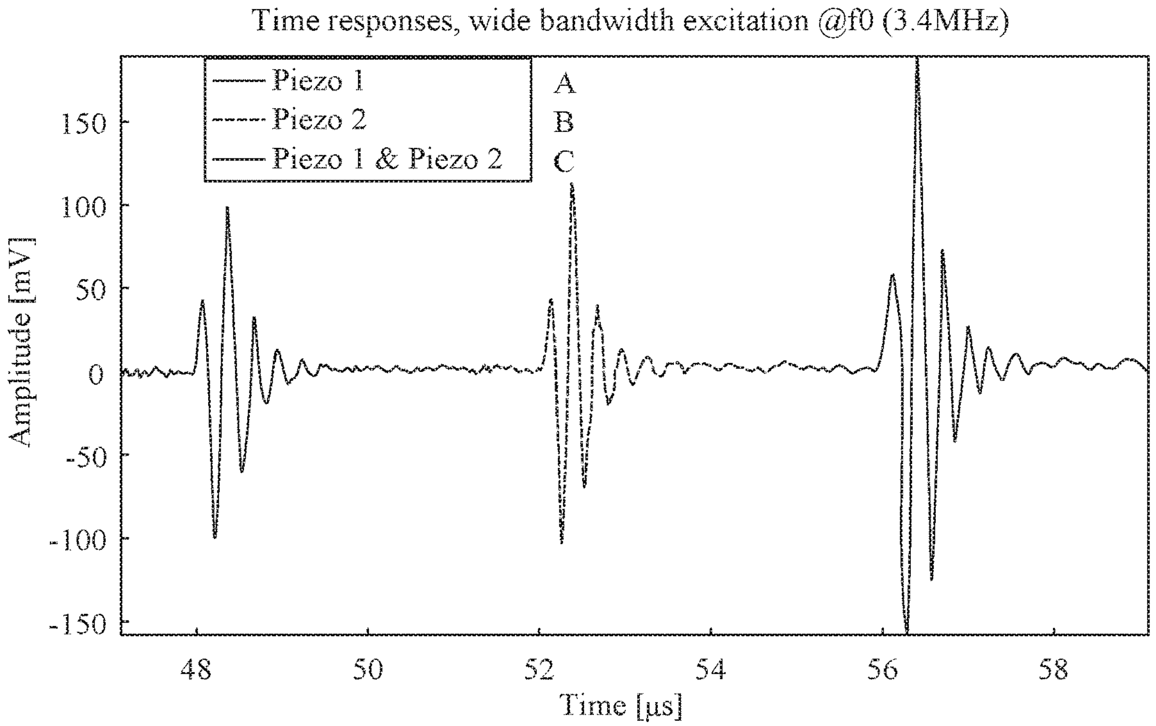
FIG. 13 and FIG. 14 are graphs illustrating the result of operation of the transducer of FIG. 9.

FIG. 13 shows the received electrical signal from the exemplary first electrode 143 (signal A); the exemplary second electrode 146 (signal B); and the elements connected together (signal C). The time scale is not absolute as each signal has been delayed from the others only for clarity purpose. The amplitude of signal C is twice the amplitude of signal A and signal B since only half of the piezoelectric thickness is involved in the mechanical to electrical conversion for signal A and signal B in this exemplary embodiment. Provided the opposite poling directions, p, of the two piezoelectric layers 132 and 134, signals from the exemplary first electrode 143 and from the exemplary second electrode 146 add up to obtain signal C. On the opposite, if the two piezoelectric layers 132 and 134 exhibit the same poling direction, p, then signal A will be roughly the opposite of signal B, therefore the sum of these signals (signal C) will be roughly zero.

Figure 14:
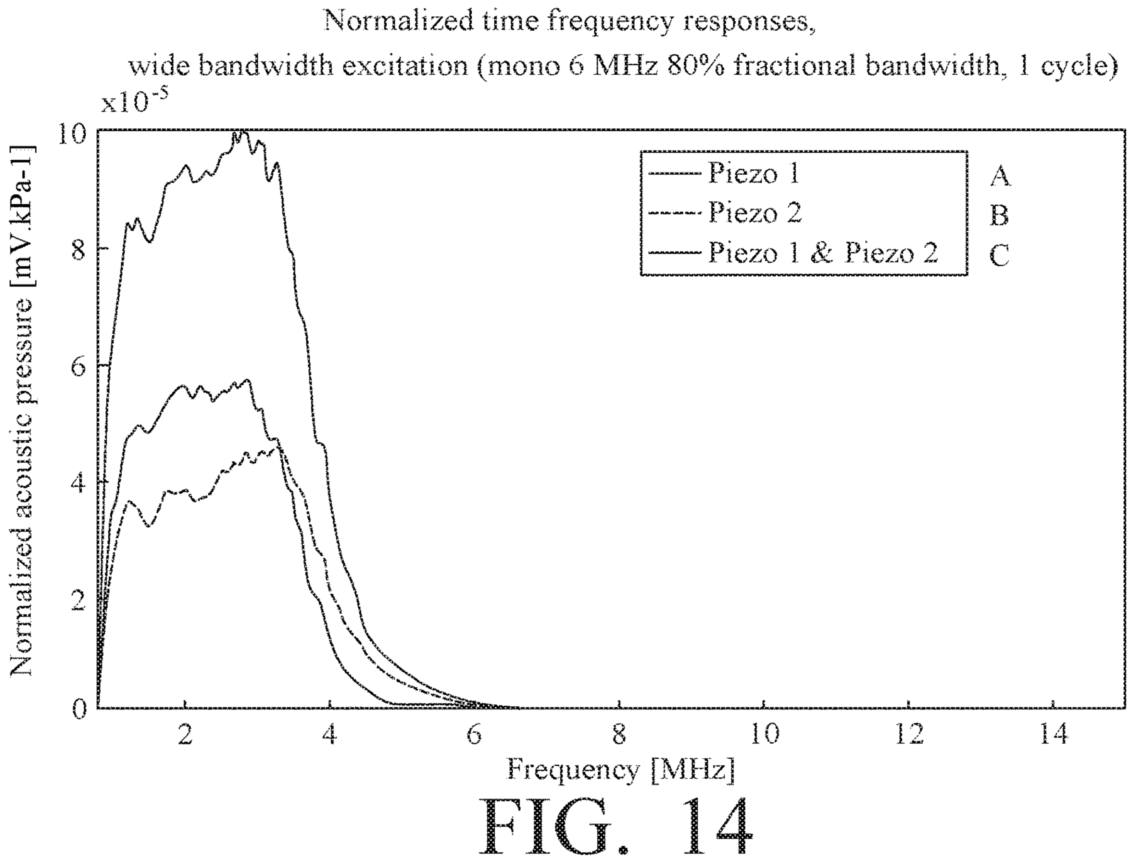

FIG. 14 shows the same measured signals as in FIG. 13 in the frequency domain. The central frequency and the bandwidth is the same for signal A, signal B, and signal C, showing that the transducer operates at the same half-wavelength mode.

Therefore, the abovementioned measurement results of this exemplary embodiment show that each element can be operated independently with a common ground voltage reference. Moreover both bottom and top electrode arrays can also be operated independently or in conjunction since the electromechanical conversion is dissociated from the common half-wavelength mode. With such degree of freedom, one array can be, for example, dedicated to receive and the other one to transmit during the same Tx/Rx sequence, thus avoiding near-field blinding in the resulting image. Moreover as each element is operated independently in both array directions, beam forming techniques can be applied.

Moreover, whatever the array of electrodes activated in transmit, this exemplary embodiment has the advantage of allowing immediate reception on both arrays instead of transmitting and receiving in separated arrays as for conventional RCA transducers.

It is noted that the common ground electrode 136 is connected to a first braid 143b of the first coaxial cable 143 and to a second braid **145*b* of the second coaxial cable 145** for proper transmission through the cables in both transmit and receive modes, which is necessary to efficiently convey high frequency electrical signals through the cables (between 1 m to 2.5 m on average).

In FIG. 9 through FIG. 14, this original method of operation has been described with respect to a single element transducer where electrodes of each layer are identical in dimension and position. For an RCA transducer, the same method of operation is used by controlling the amplitude, the frequency, and the phase of each transducer element to properly steer and apodize a pressure wave (i.e., beam) in transmit. In receive, software or hardware beamformation strategies are used within the imaging system 124.

Figure 15:
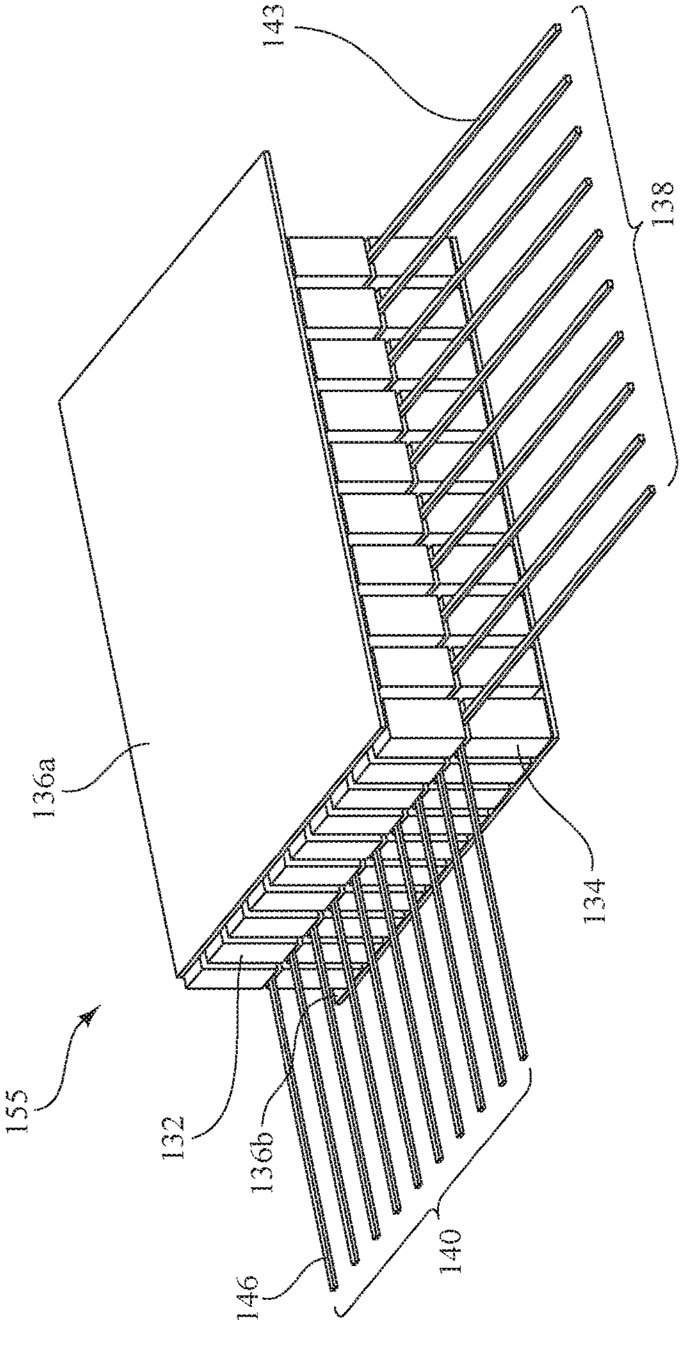
FIG. 15 is a schematic perspective of an exemplary stacked architecture transducer where the ground electrodes are externally positioned enhancing the electromagnetic (EM) shielding.
Figure 16:
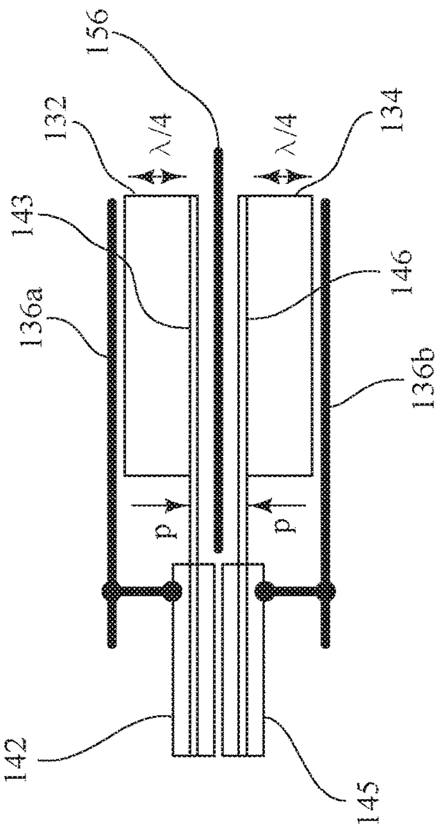
FIG. 16 is a schematic diagram of a single element transducer of the exemplary stacked architecture transducer of FIG. 15.

FIG. 15 and FIG. 16 show another exemplary embodiment 155 of the invention, where a first ground electrode **136*a* is on an outer face of the first piezoelectric layer 132, and a second ground electrode 136b is on an outer face of the second piezoelectric layer 134. Thus, the common ground electrodes 136a, 136b are positioned on the external faces of the stack. The first array of electrodes 138 and the second array of electrodes 140 are positioned between the first piezoelectric layer 132 and the second piezoelectric layer 134 at a first orientation angle (90 degrees in the exemplary embodiment, but not limited thereto), and with a first inner insulation layer 156 to electrically insulate the first array of electrodes 138 from the second array of electrodes 140. This can be done by using a flexible organic printed circuit or a mineral layer using additive or bonding technics. Such an architecture allows improved electromagnetic (EM) shielding by presenting the common ground electrodes 136***a*, 136*b* to external parasitic noises. The inner insulation layer 156 can also significantly improve the thermal dissipation if it is highly thermally conductive or thick. The first inner insulation layer 156 also plays a mechanical role in the transducer electromechanical behavior.

Figure 17:
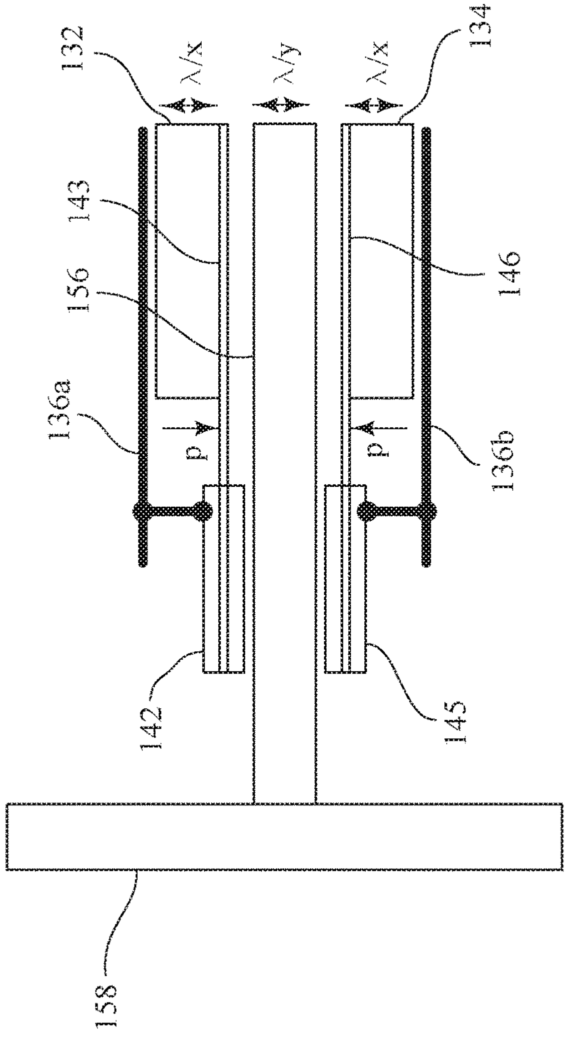
FIG. 17 is a schematic diagram of a single element transducer of a variation of the exemplary stacked architecture transducer of FIG. 15 where the inner insulation layer is chosen to enhance the thermal dissipation within the RCA stack and can be improved when thermally connected to a heatsink.

For instance, the exemplary embodiment of FIG. 17 shows the same architecture described in FIG. 15 and FIG. 16, but with a thicker first inner insulation layer 156 that simultaneously has a mechanical and a thermal function. Its thickness could be a specific value, such as λ/4 or λ/2, but is not limited thereto. In any case, the resulting stack, including the passive material and the piezoelectric layers, is operated along the same half-wavelength mode centered around f0 so that $2\lambda/x+\lambda/y=(2n+1)\lambda/2$. The inner conductive material is then thermally connected to a heatsink 158 allowing a better thermal management of the transducer.

Figure 18:
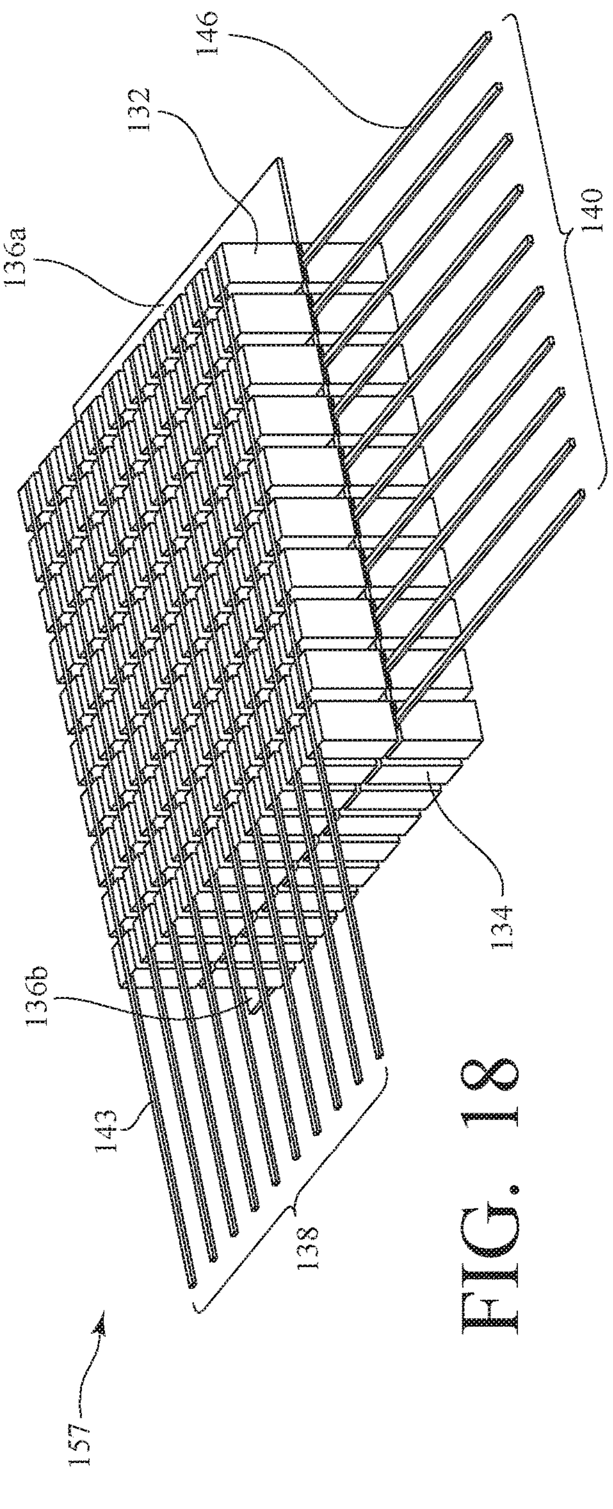
FIG. 18 is a schematic perspective of an exemplary stacked architecture transducer with a non-symmetrical arrangement of the layers.
Figure 19:
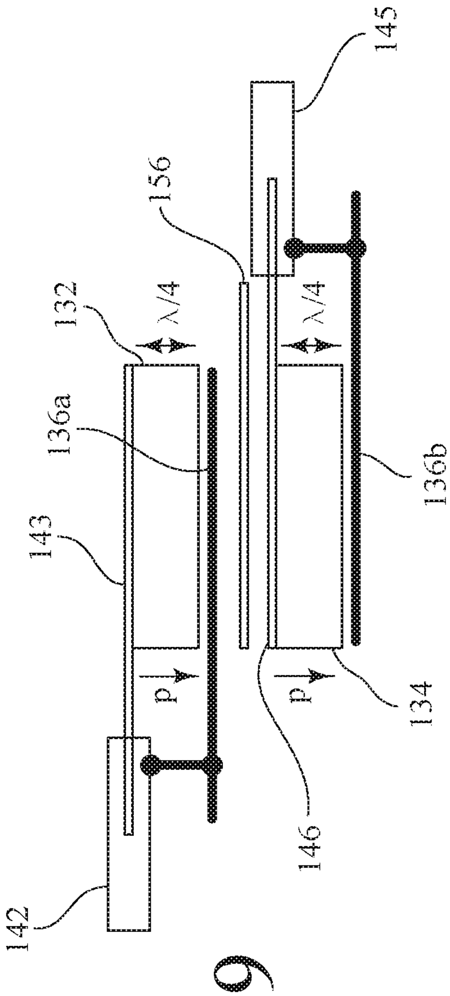
FIG. 19 is a schematic diagram of a single element transducer of the exemplary stacked architecture transducer of FIG. 19.

FIG. 18 and FIG. 19 show another exemplary embodiment 157 of the invention having the same polarization direction on each piezoelectric layer. This architecture allows manufacturing such a transducer through a different assembly and process flow making such a transducer manufacture and assembly easier. For instance, this architecture allows processing (plating, element singulation, cleaning and coating, etc.) each layer sequentially from the bottom to the top of the entire stack without having to separately process each piezoelectric layer and perform a final assembly step. In this embodiment, the first piezoelectric layer 132 is provided with the first array of electrodes 138 on its outer surface (i.e., outer face) and the first ground electrode 136*a* at its inner surface. The second piezoelectric layer 134 is provided with the second array of electrodes 140 on its inner surface and the second ground electrode 136*b* on its outer surface. The first inner insulation layer 156 is positioned between the first ground electrode 136*a* and the second array of electrodes 140. The piezoelectric layers 132, 134 are stacked to form a stack of piezoelectric layers having poling directions oriented in the same direction. Therefore, a signal applied to the exemplary first electrode 143 yields to the same deformation (contraction or dilatation) of the first piezoelectric layer 132 as of the second piezoelectric layer 134 when the same voltage is applied to the exemplary second electrode 146.

FIG. 20 through FIG. 23 show other exemplary embodiments using different electrode orientations by adding uneven and even numbers of piezoelectric layers.

Figure 20:
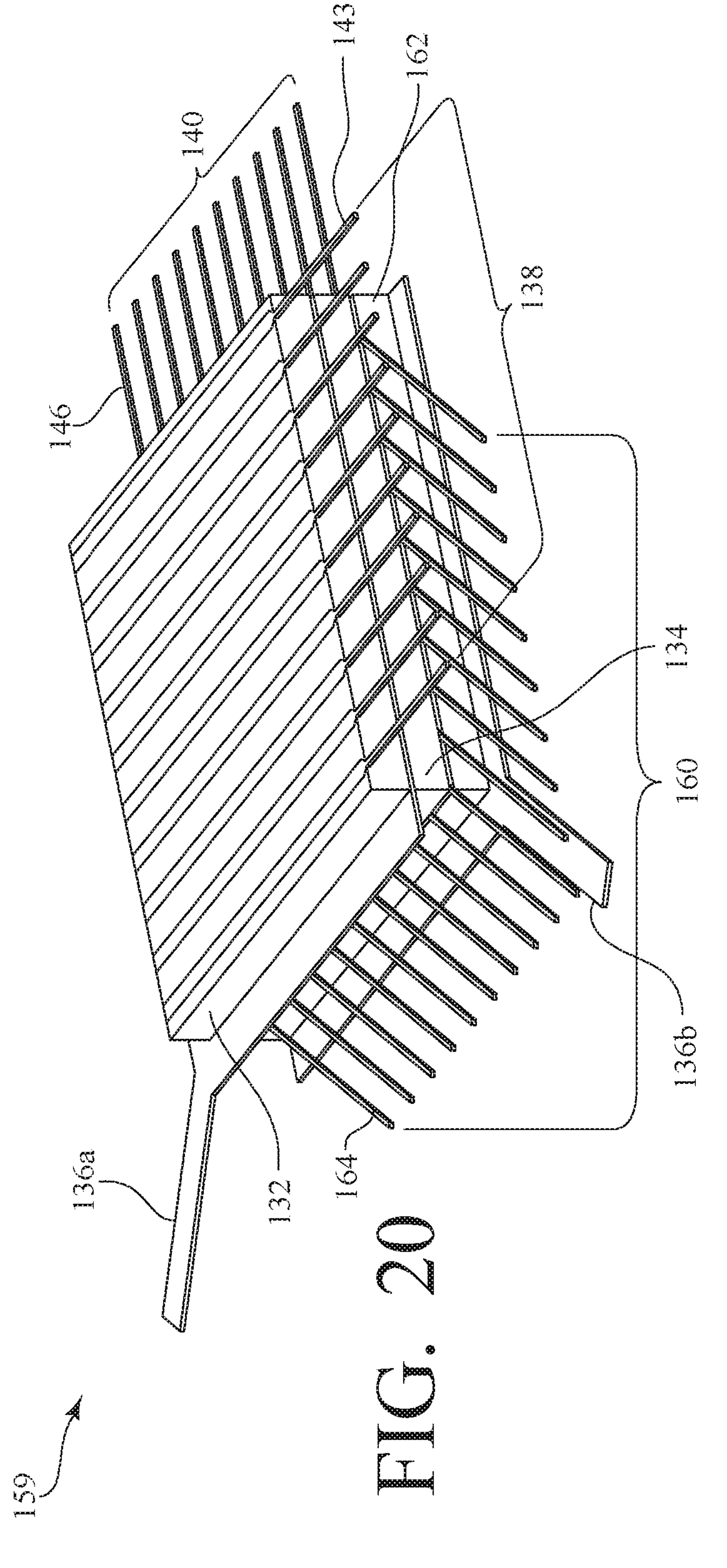
FIG. 20 is a schematic perspective of an exemplary stacked architecture transducer with an uneven number of piezoelectric layers.
Figure 21:
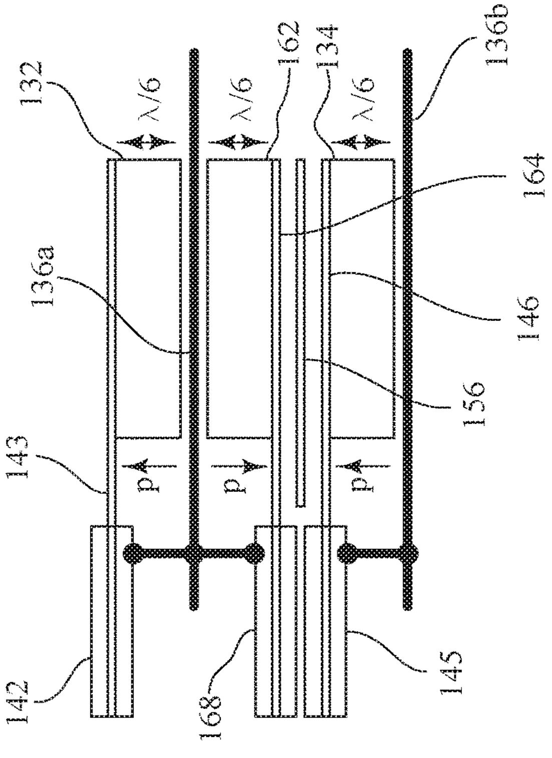
FIG. 21 is a schematic diagram of a single element transducer of the exemplary stacked architecture transducer of FIG. 20.

In the exemplary embodiment 159 shown in FIG. 20 and FIG. 21, a third array of electrodes 160 oriented at a second orientation angle other than the first orientation angle (in the exemplary embodiment shown, the first orientation angle is 90 degrees and the second orientation angle is 45 degrees) to the first array of electrodes 138 is patterned on a third piezoelectric layer 162. Each of the three piezoelectric layer 132, 134, 162 exhibit a thickness equal to a sixth of the wavelength, so that the entire thickness of the assembly is kept to one-half half of a wavelength. Thus, the resulting stack comprising the first piezoelectric layer 132, the second piezoelectric layer 134, and the third piezoelectric layer 162 still operates at f0. FIG. 21 shows a schematic of a single transducer element of the embodiment, including the exemplary first electrode 143, the exemplary second electrode 146, and an exemplary third electrode 164 in respective electrical communication with the first coaxial cable 142, the second coaxial cable 145, and a third coaxial cable 168. All the individual piezoelectric layers are excited at f0 excitation corresponding to the stationary wave frequency of the entire stack thickness. In reception, the acoustic signal waveforms correspond to those obtained with the total piezoelectric assembly, resulting in received signals centered at f0. The received signals are then independently beam formed using hardware or software approaches similarly to the two layer stacked approach. This arrangement is applicable to any transducer having an odd number of piezoelectric layers of three or more (e.g., 3, 5, 7, or 9 piezoelectric layers).

Figure 22:
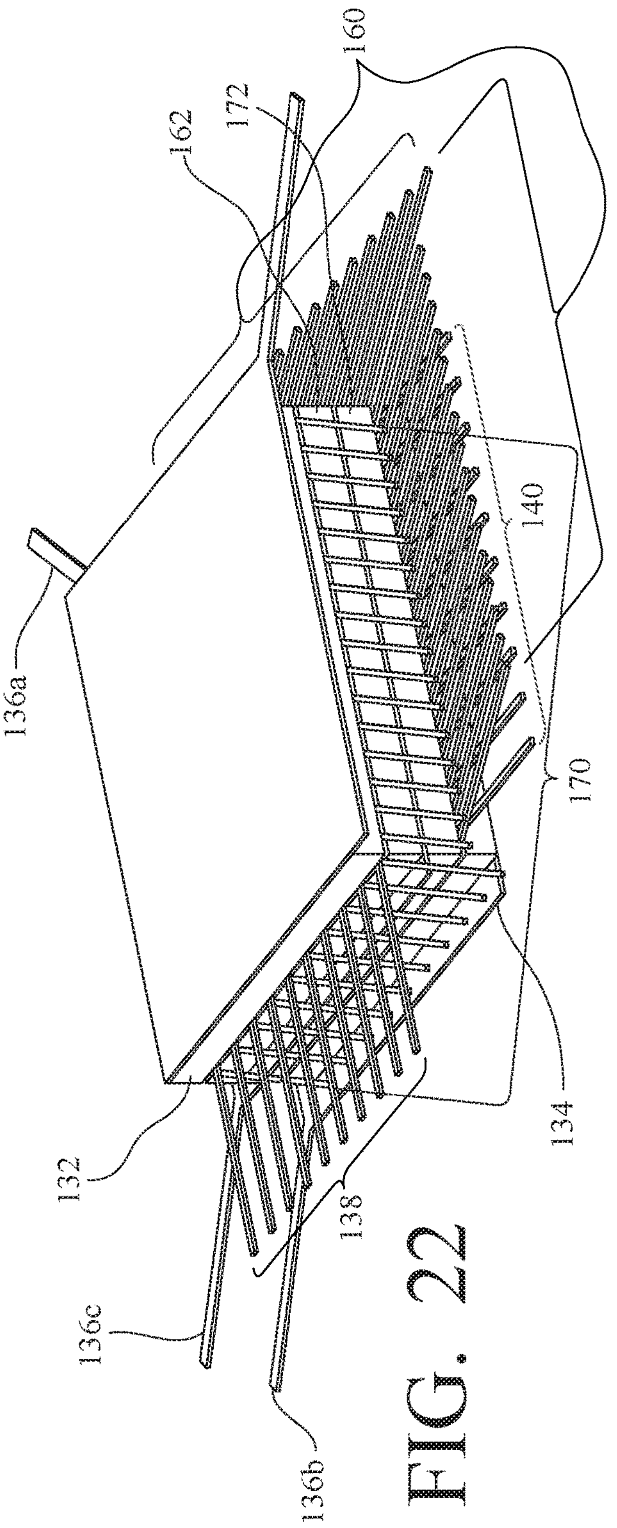
FIG. 22 is a schematic perspective of an exemplary stacked architecture transducer with an even number of piezoelectric layers.
Figure 23:
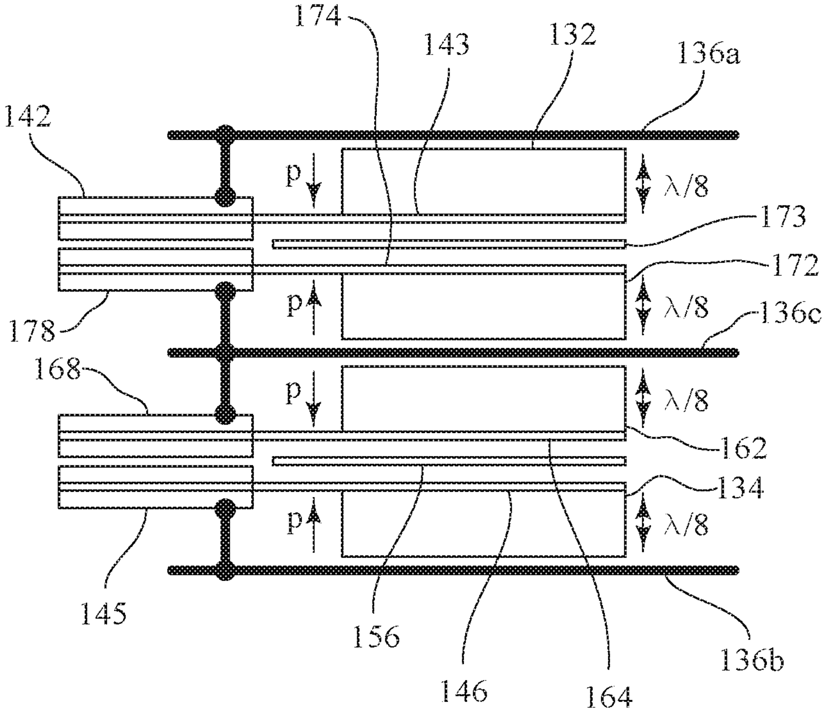
FIG. 23 is a schematic diagram of a single element transducer of the exemplary stacked architecture transducer of FIG. 22.

In the exemplary embodiment 169 shown in FIG. 22 and FIG. 23, a fourth array of electrodes 170 is patterned on a fourth piezoelectric layer 172. The fourth array of electrodes 170 is oriented at a third orientation angle to the first array of electrodes 138 different from the first orientation angle and the second orientation angle (in the exemplary embodiment shown, the first orientation angle is 90 degrees, the second orientation angle is 30 degrees, and the third orientation angle is 60 degrees). Each of the piezoelectric layers has a thickness equal to an eighth of the wavelength, so that the resulting stack still has a thickness of a half-wavelength and still operates at f0. Common ground electrodes 136a, 136b, and 136c are positioned on the external faces of the stack and in the middle of the stack, as shown. A first inner insulation layer 156 is positioned between the second array of electrodes 146 (including the second exemplary electrode 146) and the third array of electrodes 160 (including the third exemplary electrode 164), and a second inner insulation layer 173 is positioned between the fourth array of electrodes 170 (including fourth exemplary electrode 174) and the first array of electrodes 138 (including first exemplary electrode 143). This arrangement is applicable to any transducer having an even number of piezoelectric layers of four or more.

In both cases (even or odd number of piezoelectric layers), it is possible to better control the beam shape, apodization and steering by controlling the phase, the frequency and the amplitudes of each element of the different arrays. In receive, through the same imaging aperture, the backscattered information received is enriched and coherent hardware or software beamformation techniques can be applied since the backscattered information has been expressed on the whole stack thickness and aperture. This gives key advantages for 3D imaging because such a stacked approach would allow considerably enrichment of the information during the image formation since the triangulation of the backscattered information will be made with additional dimensions but within the same acoustic aperture.

Figure 24:
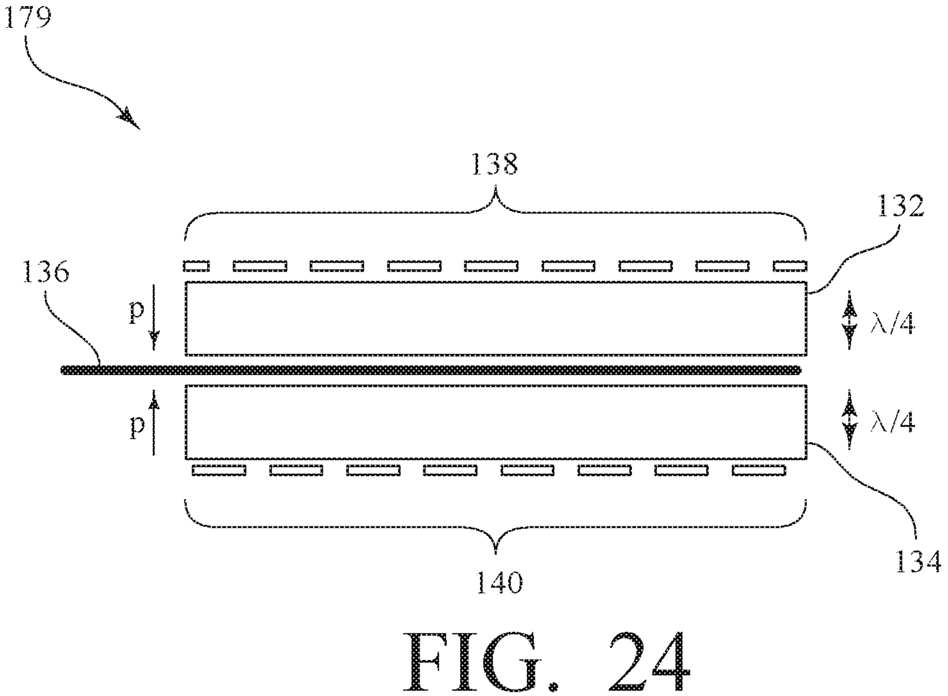
FIG. 24 is a schematic diagram of an exemplary 1D stacked array having interleaved electrodes oriented along a same direction.

In FIG. 24, an embodiment 179 is shown where the first array of electrodes 138 and the second array of electrodes 140 are aligned along the same direction (i.e., the first orientation angle is 0 degrees) but with a different pattern (e.g., the second array of electrodes 140 is offset from the first array of electrodes 138).

Although the previous exemplary embodiments relate to row-column array configurations, the exemplary embodiments hereinafter advantageously rely on the same piezoelectric layer stacking principle but with other electrode configurations.

Figure 25:
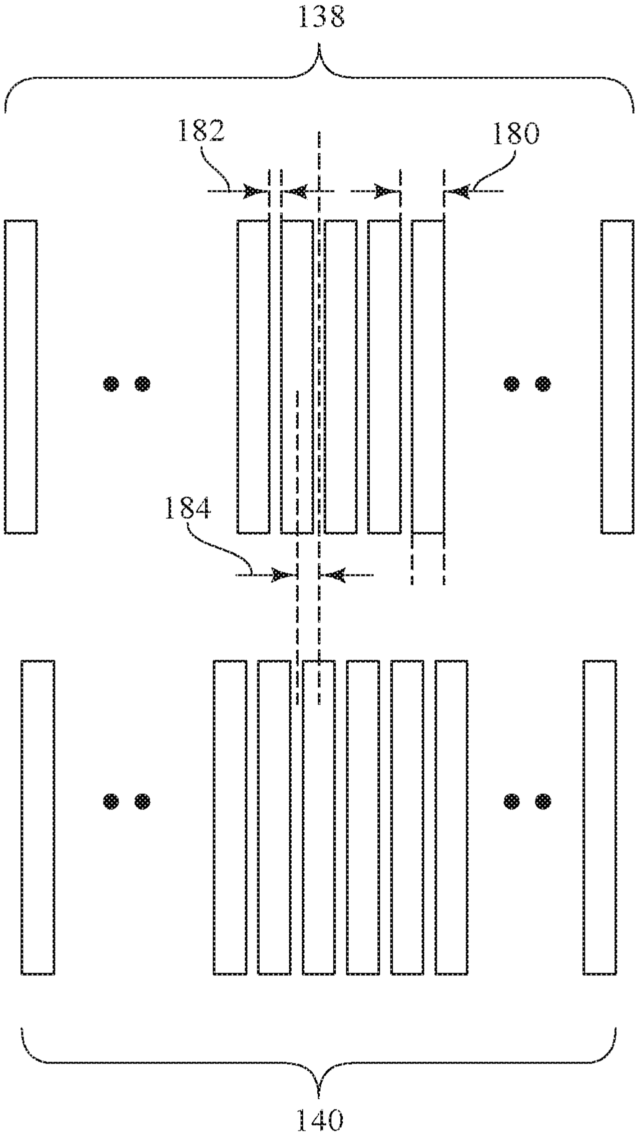
FIG. 25 is a schematic diagram of an arrangement of two interleaved rectilinear arrays of electrodes, such as in the embodiment of FIG. 24.

FIG. 25 is a schematic diagram showing an arrangement of two interleaved rectilinear arrays of electrodes, such as in the embodiment of FIG. 24. In this exemplary embodiment, the arrays of electrodes 138 and 140 exhibit the same pitch 180 and kerf 182 properties tuned with regards to imaging objectives. The first array of electrode 138 is offset from the second array of electrode 140 by half of the pitch 180. This configuration is equivalent to one single array with a pitch equal to 184 but has the advantage to exhibit larger element surface and/or a larger pitch for each electrode array. This is particularly advantageous for very fine pitch array. As a result, it is possible to reduce side lobes and grating lobes issues and improve the image quality even at high deflection angles.

Whereas this exemplary embodiment has electrode arrays with the same pitch, it is obvious for the one skilled in the art to have the two electrode arrays with different pitches, numbers of elements, and dimensions of elements, so that the two transducer arrays are interleaved. This further allows pulling away or even suppress grating and side lobes, and allows larger beam deflection for wider sectorial imaging or better spatial compounding strategies.

Figure 26:
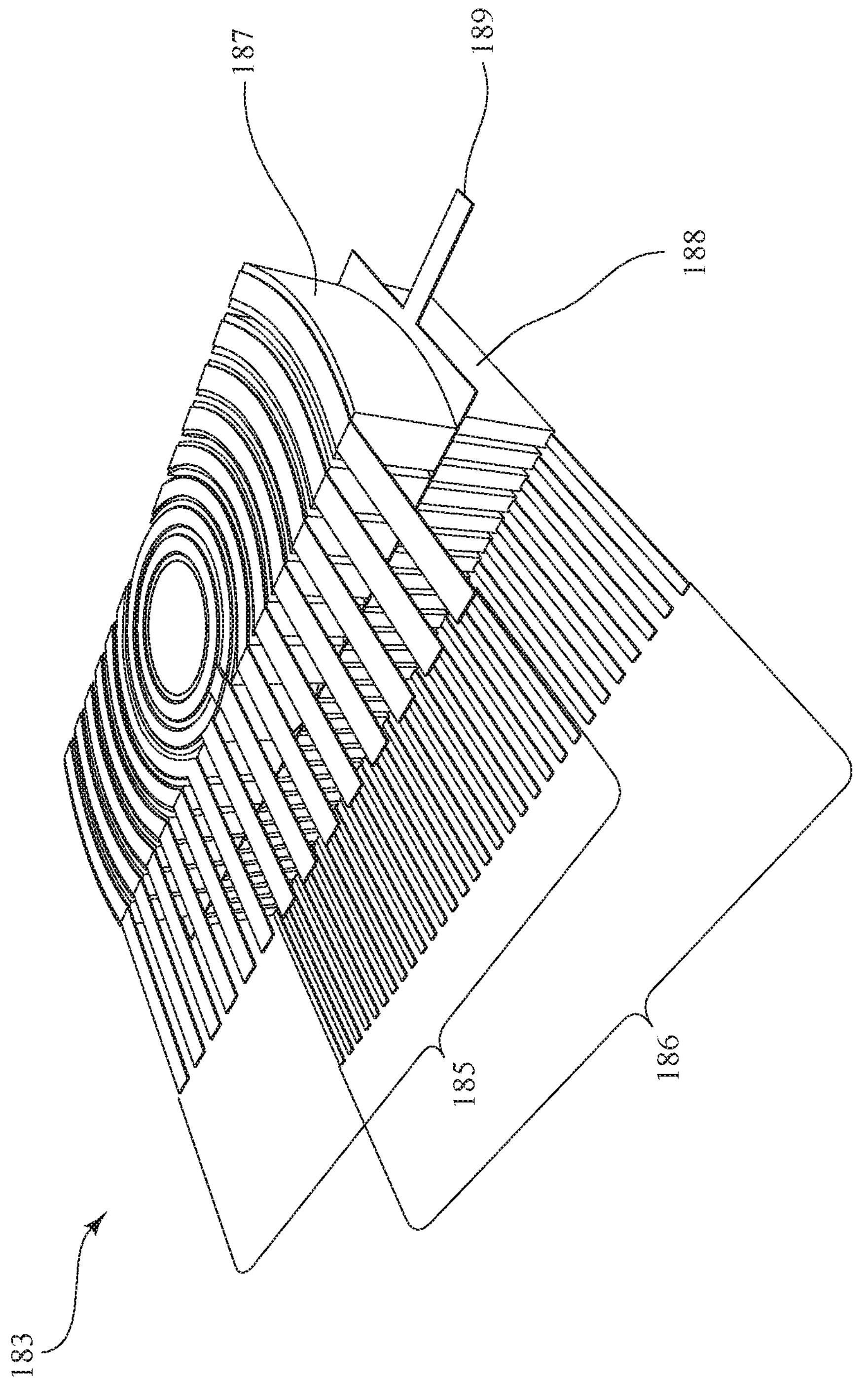
FIG. 26 is a schematic diagram of an exemplary stacked architecture transducer with a top piezoelectric layer having an array of coaxial, semi-cylindrical curved electrodes and a bottom piezoelectric layer having an array of parallel, linear electrodes.

FIG. 26 is a schematic diagram of another exemplary embodiment 183 with a top piezoelectric layer 187 (i.e., the first piezoelectric layer) having an array of coaxial, semi-cylindrical curved electrodes 185 (i.e., the first array of electrodes), a bottom piezoelectric layer 188 (i.e., the second piezoelectric layer) having an array of parallel, linear electrodes 186, and an inner common ground electrode 189 (i.e., the first ground electrode and the second ground electrode) between the top piezoelectric layer 187 and the bottom piezoelectric layer 188. Advantageously, having multiple layers also allows the mixing of rectilinear and annular arrays of electrodes within a same active aperture. Such array combinations enable apodization and focalization capabilities within a transducer. This embodiment includes a different array organization (rectilinear, annular, etc.) used within the same stack architecture for apodization or beam focalization.

REFERENCES

[R1]—"A Dual-Layer Transducer Array for 3-D Rectilinear Imaging", Jesse T. Yen, Member, IEEE, Chi Hyung Seo, Student Member, IEEE, Samer I. Awad, and Jong S. Jeong, Student Member, IEEE, IEEE Transactions on Ultrasonics, Ferroelectrics, and Frequency Control, vol. 56, no. 1, January 2009.

[R2]—A. W. Joyce and G. R. Lockwood, "Crossed-array transducer for real-time 3D imaging," IEEE Int. Ultrason. Symp. IUS, pp. 2116-2120, 2014.

[R3]—A. Cochran, V. Murray and G. Hayward, "Multilayer piezocomposite ultrasonic transducers operating below 50 kHz", Proc. 1999 IEEE Ultrasonics Symposium (1999) 953-956.

what is claimed is:

1. An ultrasound transducer comprising:

a first piezoelectric layer stacked on at least a second piezoelectric layer to form a stack;

the first piezoelectric layer having one major face metallized and patterned to form a first array of coaxial, semi-annular electrodes and the other major face metallized to form a first ground electrode for operation as a first transducing system;

the second piezoelectric layer having one major face metallized and patterned to form a second array of parallel linear electrodes and the other major face metallized to form a second ground electrode for operation as a second transducing system, the second piezoelectric layer having a thickness such that an overall thickness of the stack is equal to an uneven number of half-wavelengths of an acoustic wave to be generated when the first piezoelectric layer and the second piezoelectric layer are independently operated;

an acoustic impedance adaptation layer positioned directly on one side of the stack;

an acoustic damping layer positioned on the other side of the stack; and a stiffener positioned on the acoustic damping layer.

* * * * *